United States Patent
Hellyer et al.

(10) Patent No.: US 8,420,320 B2
(45) Date of Patent: *Apr. 16, 2013

(54) METHOD FOR RAPID IDENTIFICATION OF MICROORGANISMS

(75) Inventors: Tobin J. Hellyer, Westminster, MD (US); James Nadeau, Cockeysville, MD (US); Jianrong Lou, Boyds, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 87 days.

This patent is subject to a terminal disclaimer.

(21) Appl. No.: 12/643,430

(22) Filed: Dec. 21, 2009

(65) Prior Publication Data

US 2010/0311607 A1 Dec. 9, 2010

Related U.S. Application Data

(63) Continuation of application No. 11/197,594, filed on Aug. 5, 2005, now Pat. No. 7,662,562.

(60) Provisional application No. 60/599,858, filed on Aug. 10, 2004.

(51) Int. Cl.
  *C12Q 1/68* (2006.01)
  *C07H 21/04* (2006.01)

(52) U.S. Cl.
  USPC ...................... 435/6.11; 536/24.32

(58) Field of Classification Search .......... None
  See application file for complete search history.

(56) References Cited

U.S. PATENT DOCUMENTS

| | | | | |
|---|---|---|---|---|
| 4,563,419 | A | * | 1/1986 | Ranki et al. ............... 435/6.12 |
| 6,110,678 | A | * | 8/2000 | Weisburg et al. ............ 435/6.12 |
| 2002/0081588 | A1 | | 6/2002 | De Lumley-woodyear et al. |
| 2003/0105320 | A1 | * | 6/2003 | Becker et al. ............... 536/24.3 |

FOREIGN PATENT DOCUMENTS

| WO | 0070086 A1 | | 11/2000 |
|---|---|---|---|
| WO | WO 00/70086 | * | 11/2000 |
| WO | 0210444 A1 | | 2/2002 |
| WO | 02/094868 A2 | | 11/2002 |
| WO | 2004/046385 A1 | | 6/2004 |

OTHER PUBLICATIONS

Chandler et al., "Sequence Versus Structure for the Direct Detection of 16S rRNA on Planar Oligonucleotide Microarrays," Applied and Environmental Microbiology, 2003; 69(5):2950-2958.

Gabig-Ciminska et al., "Electric Chips for Rapid Detection and Quantification of Nucleic Acids," Biosensors and Bioelectronics, 2004; 19:537-546.

Hellyer et al., "Quantitative Analysis of mRNA as a Marker for Viability of Mycobacterium tuberculosis," Journal of Clinical Microbiology, Vo. 37, No. 2, pp. 290-295, 1999.

Hogardt et al., "Specific and Rapid Detection by Fluorescent in Situ Hybridization of Bacteria in Clinical Samples Obtained from Cystic Fibrosis Patients." Journal of Clinical Microbiology, vol. 38, No. 2, pp. 818-825, 2002.

Shah et al., "Novel, Ultrasensitive, Q-Beta Replicase-Amplified Hybridization Assay for Detection of Chlamydia trachomatis," Journal of Clinical Microbiology, 1994; 32(11):2718-2724.

Small et al., "Direct Detection of 16S rRNA in Soil Extracts by Using Oligonucleotide Microarrays," Applied and Environmental Microbiology, 2001; 67(10):4708-4716.

Smith et al., "Comparison of Biosequences," Advances in Applied Mathematics, vol. 2, pp. 482-489, 1981.

Weinstein et al., "The Clinical Significance of Positive Blood Cultures: A Comprehensive Analysis of 500 Episodes of Bacteremia and Fungemia in Adults. I. Laboratory and Epidemiologic Observations," Reviews of Infectious Diseases, vol. 5, No. 1, pp. 35-53, 1983.

Zakrzewska-Czerwinska J et al., "Identification of *Staphylococcus epidermidis* Using a 16S rRNA-directed Oligonucleotide Probe," Fems. Microbiology Letters, 1992, vol. 79, No. 1-3, pp. 51-58, 1992.

* cited by examiner

*Primary Examiner* — Amanda Haney
(74) *Attorney, Agent, or Firm* — Lerner, David, Littenberg, Krumholz & Mentlik, LLP

(57) ABSTRACT

The present invention relates, in general, to probes, methods, and kits used to determine the presence or absence of a microorganism in a sample. The probes, methods, and kits comprise at least one capture probe and/or at least one detector probe.

26 Claims, 11 Drawing Sheets

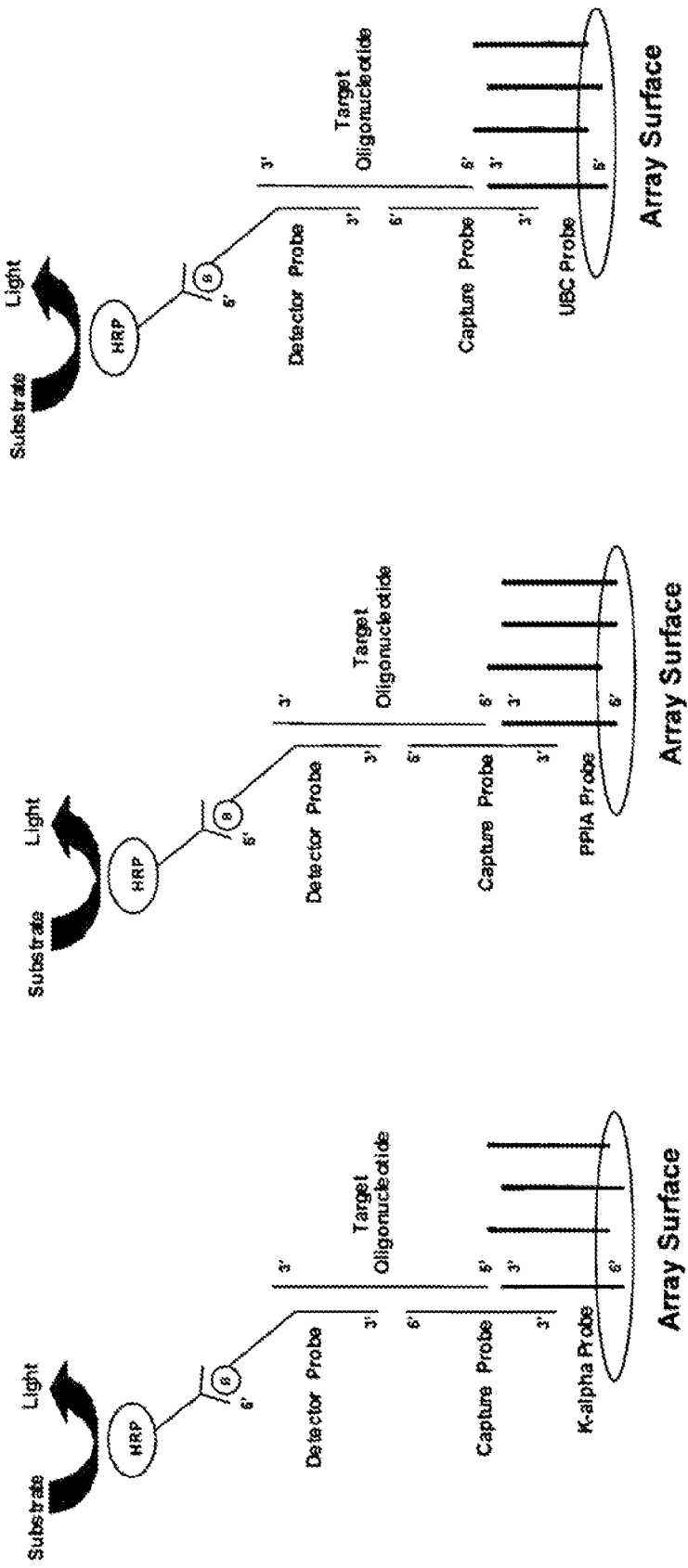

FIGURE 6

| Organism | Oligonucleotide | 5'-3' Sequence |
|---|---|---|
| E. coli | Synthetic Target Oligonucleotide (SEQ ID No. 54) | TCC C<u>TA GCC TCC GCT CTT AGG A</u>TA AAG ACT GAC TAA GCA TGT AGT ACC GAG GAT SEQ ID No. 57 |
| | Capture Probe (SEQ ID No. 55) | <u>TCC TCG GTA CTA CAT GCT TAG TAC ATT CAA CAG AAT CCA CAA CCT CCT CAT</u> A SEQ ID No. 59 |
| | Detector probe (SEQ ID No. 56) | Biotin-CAC TAC GAC TCT CGG TCT GAT TCT ATT TGC [TCC TAA GAG CGG AGG CTA] SEQ ID No. 7 |
| S. aureus | Synthetic Target Oligonucleotide (SEQ ID No. 60) | AAG TCT GTT TAG AAG AAA CTT AAT C<u>AA</u> ACT AGC ATC ATG TT[G GTT GTT TAT CAC TTT TCA TGA] TGC SEQ ID No. 64 |
| | Capture Probe (SEQ ID No. 61) | <u>TTG ATT AAG TTT CTT CTA AAC AGA</u> TAC A*TC ATA ATC ATA AAC TTA ACT CTG CAA TCC* A SEQ ID No. 65 |
| | Detector probe (SEQ ID No. 62) | Biotin-CAC TAC GAC TCT CGG TCT GAT TCT ATT TGC [TCA TGA AAA GTG ATA AAC AAC C] SEQ ID No 2 |
| S. epidermidis | Synthetic Target Oligonucleotide (SEQ ID No. 66) | AAC ACA TTT CGG TTA AAT ATA ACT GAC AGT ATC ATG TTG G[TT GTT TAT TGC TTA GCA TGA TGC] GA SEQ ID No. 70 |
| | Capture Probe (SEQ ID No. 67) | <u>CAG TTA TAT TTA ACC GAA ATG TGT</u> *ACA GAA AGT GCA ATG AAA TTT GTT GAA ACC TTA* SEQ ID No. 71 |
| | Detector probe (SEQ ID No. 68) | Biotin- CAC TAC GAC TCT CGG TCT GAT TCT ATT TGC [CAT CAT GCT AAG CAA TAA ACA A] SEQ ID No. 8 |

Regions of complementarity between the Target and Capture Probes are underlined
Regions of complementarity between the Target and Detector Probes are in boxes
Italicized text corresponds to human gene sequences: *E. coli*, K-alpha; *S. aureus*, PPIA; *S. epidermis*, UBC FIGURE 7
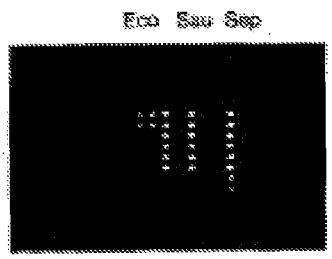
FIGURE 7A
| Eco | Sau | Sep | Staining |
|---|---|---|---|
| + | + | + | + |
| 352,695 | 381157 | 400507 | 209063 |
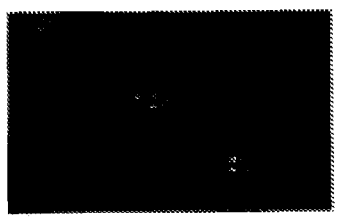
FIGURE 7B
| Eco | Sau | Sep | Staining |
|---|---|---|---|
| - | - | - | + |
| 125 | 185 | 223 | 116131 |
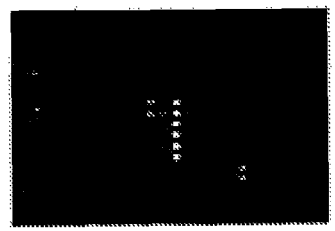
FIGURE 7C
| Eco | Sau | Sep | Staining |
|---|---|---|---|
| + | - | - | + |
| 377836 | 227 | 143 | 207125 |
FIGURE 7D
| Eco | Sau | Sep | Staining |
|---|---|---|---|
| - | + | - | + |
| 2223 | 380644 | 183 | 189789 |
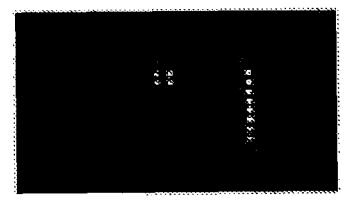
FIGURE 7E
| Eco | Sau | Sep | Staining |
|---|---|---|---|
| - | - | + | + |
| 224 | 283 | 392900 | 210015 |
Eco = *E. coli*
Sau = *S. aureus*
Sep = *S. epidermis*
Staining = biotinylated beta-actin positive control

FIGURE 7F

Location of immobilization probes

|   | 1 | 2 | 3 | 4 | 5 | 6 | 7 | 8 |
|---|---|---|---|---|---|---|---|---|
| A | Staining | Staining | K-alpha | ActB | PPIA | GAPD | RPS5 | UBC |
| B | Staining | Staining | K-alpha | ActB | PPIA | GAPD | RPS5 | UBC |
| C | Buffer | Buffer | K-alpha | ActB | PPIA | GAPD | RPS5 | UBC |
| D | Buffer | Buffer | K-alpha | ActB | PPIA | GAPD | RPS5 | UBC |
| E | Buffer | Buffer | K-alpha | ActB | PPIA | GAPD | RPS5 | UBC |
| F | Buffer | Buffer | K-alpha | ActB | PPIA | GAPD | RPS5 | UBC |
| G | Buffer | Buffer | Buffer | Buffer | Buffer | Buffer | Buffer | Staining |
| H | Buffer | Buffer | Buffer | Buffer | Buffer | Buffer | Buffer | Staining |

K-alpha = tubulin alpha-1
ActB = beta-actin
PPIA = peptidylprolyl isomerase A
GAPD = glyceraldehydes-3-phosphate dehydrogenase
RPS5 = disease resistance protein RPS5
UBC = ubiqitinin-conjugating enzyme E2A
Staining = biotinylated beta-actin oligonucleotide (SEQ ID No. 83)

Location of specific Capture Probes

|   | 1 | 2 | 3 | 4 | 5 | 6 | 7 | 8 |
|---|---|---|---|---|---|---|---|---|
| A | Staining | CP1 | CP2 | CP4 | CP5 | CP7 | CP8 | Buffer |
| B | Staining | CP1 | CP2 | CP4 | CP5 | CP7 | CP8 | Buffer |
| C | Buffer | CP1 | CP3 | CP4 | CP6 | CP7 | CP9 | Staining |
| D | Buffer | CP1 | CP3 | CP4 | CP6 | CP7 | CP9 | Staining |
| E | Buffer | CP2 | CP3 | CP5 | CP6 | CP8 | CP9 | Staining |
| F | Buffer | CP2 | CP3 | CP5 | CP6 | CP8 | CP9 | Staining |

Buffer: Negative control with no oligonucleotide spotted
Staining: Spotted with biotin-labeled oligonucleotide as control for detection reagents

FIGURE 8B

Target RNA: *E. coli*

Detector Probes: *E. coli* ssrA (DP1); *E. coli* rnp (DP4); *E. coli* 16S rRNA (DP7)

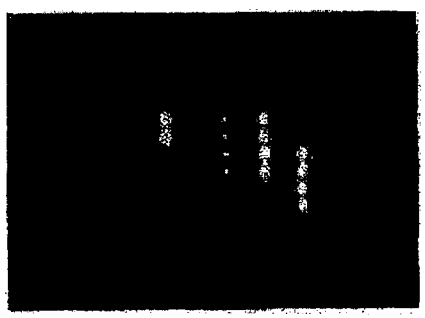

Target RNA: *S. aureus* and *S. epidermidis*

Detector Probes: *E. coli* ssrA (DP1); *E. coli* mp (DP4); *E. coli* 16S rRNA (DP7)

Target RNA: *S. aureus*

Detector Probes: *S. aureus* ssrA (DP2); *S. aureus* mp (DP5)

Target RNA: *E. coli* and *S. epidermidis*

Detector Probes: *S. aureus* ssrA (DP2); *S. aureus* rnp (DP5)

SEQUENCE LISTING

```
<160> NUMBER OF SEQ ID NOS: 87

<210> SEQ ID NO 1
<211> LENGTH: 24
<212> TYPE: DNA
<213> ORGANISM: Staphylococcus aureus

<400> SEQUENCE: 1
ttgattaagt ttcttctaaa caga                                           24

<210> SEQ ID NO 2
<211> LENGTH: 22
<212> TYPE: DNA
<213> ORGANISM: Staphylococcus aureus

<400> SEQUENCE: 2
tcatgaaaag tgataaacaa cc                                             22

<210> SEQ ID NO 3
<211> LENGTH: 19
<212> TYPE: DNA
<213> ORGANISM: Escherichia coli

<400> SEQUENCE: 3
aattcctacg tcctcggta                                                 19

<210> SEQ ID NO 4
<211> LENGTH: 17
<212> TYPE: DNA
<213> ORGANISM: Escherichia coli

<400> SEQUENCE: 4
tacattcgct tgccagc                                                   17

<210> SEQ ID NO 5
<211> LENGTH: 22
<212> TYPE: DNA
```

```
<213> ORGANISM: Escherichia coli

<400> SEQUENCE: 5
ctagcctgat taagttttaa cg                                              22

<210> SEQ ID NO 6
<211> LENGTH: 21
<212> TYPE: DNA
<213> ORGANISM: Escherichia coli

<400> SEQUENCE: 6
tcctcggtac tacatgctta g                                               21

<210> SEQ ID NO 7
<211> LENGTH: 18
<212> TYPE: DNA
<213> ORGANISM: Escherichia coli

<400> SEQUENCE: 7
tcctaagagc ggaggcta                                                   18

<210> SEQ ID NO 8
<211> LENGTH: 22
<212> TYPE: DNA
<213> ORGANISM: Staphylococcus epidermidis

<400> SEQUENCE: 8
catcatgcta agcaataaac aa                                              22

<210> SEQ ID NO 9
<211> LENGTH: 26
<212> TYPE: DNA
<213> ORGANISM: Staphylococcus epidermidis

<400> SEQUENCE: 9
ttgattatat ttcatctaaa cagact                                          26

<210> SEQ ID NO 10
<211> LENGTH: 24
<212> TYPE: DNA
<213> ORGANISM: Staphylococcus epidermidis

<400> SEQUENCE: 10
cagttatatt taaccgaaat gtgt                                            24

<210> SEQ ID NO 11
<211> LENGTH: 18
<212> TYPE: DNA
<213> ORGANISM: Klebsiella pneumoniae

<400> SEQUENCE: 11
attcctacat cctcggca                                                   18

<210> SEQ ID NO 12
<211> LENGTH: 20
<212> TYPE: DNA
<213> ORGANISM: Klebsiella pneumoniae

<400> SEQUENCE: 12
gtcttaagag cggaagctag                                                 20

<210> SEQ ID NO 13
<211> LENGTH: 20
<212> TYPE: DNA
```

<213> ORGANISM: Klebsiella pneumoniae

<400> SEQUENCE: 13
agcctgatta gatttaacgc                                               20

<210> SEQ ID NO 14
<211> LENGTH: 23
<212> TYPE: DNA
<213> ORGANISM: Enterococcus faecalis

<400> SEQUENCE: 14
catattgcca cttaaatctc tac                                           23

<210> SEQ ID NO 15
<211> LENGTH: 23
<212> TYPE: DNA
<213> ORGANISM: Enterococcus faecalis

<400> SEQUENCE: 15
ctgtattgct agtctggtaa gct                                           23

<210> SEQ ID NO 16
<211> LENGTH: 20
<212> TYPE: DNA
<213> ORGANISM: Enterococcus faecalis

<400> SEQUENCE: 16
acactcattt aaaggttcgc                                               20

<210> SEQ ID NO 17
<211> LENGTH: 20
<212> TYPE: DNA
<213> ORGANISM: Pseudomonas aeruginosa

<400> SEQUENCE: 17
gcttagccag ctctactgag                                               20

<210> SEQ ID NO 18
<211> LENGTH: 21
<212> TYPE: DNA
<213> ORGANISM: Pseudomonas aeruginosa

<400> SEQUENCE: 18
ttaagcagct agagcgtagt t                                             21

<210> SEQ ID NO 19
<211> LENGTH: 21
<212> TYPE: DNA
<213> ORGANISM: Streptococcus pneumoniae

<400> SEQUENCE: 19
ctcaagtcta gaaactgcga g                                             21

<210> SEQ ID NO 20
<211> LENGTH: 19
<212> TYPE: DNA
<213> ORGANISM: Streptococcus pneumoniae

<400> SEQUENCE: 20
ttattttaac agcccctcg                                                19

<210> SEQ ID NO 21
<211> LENGTH: 23
<212> TYPE: DNA

<213> ORGANISM: Streptococcus mutans

<400> SEQUENCE: 21
tgtttattta acaccgttac aat 23

<210> SEQ ID NO 22
<211> LENGTH: 20
<212> TYPE: DNA
<213> ORGANISM: Streptococcus mutans

<400> SEQUENCE: 22
tcaaactcta acgatgcgag 20

<210> SEQ ID NO 23
<211> LENGTH: 23
<212> TYPE: DNA
<213> ORGANISM: Streptococcus gordonii

<400> SEQUENCE: 23
tgttttaact tgattttgac aca 23

<210> SEQ ID NO 24
<211> LENGTH: 21
<212> TYPE: DNA
<213> ORGANISM: Streptococcus gordonii

<400> SEQUENCE: 24
caaatcaagc gagtctatca a 21

<210> SEQ ID NO 25
<211> LENGTH: 23
<212> TYPE: DNA
<213> ORGANISM: Clostridium difficile

<400> SEQUENCE: 25
ccaacttcac taatatctca cct 23

<210> SEQ ID NO 26
<211> LENGTH: 19
<212> TYPE: DNA
<213> ORGANISM: Clostridium difficile

<400> SEQUENCE: 26
gtccagtctt agtcggcag 19

<210> SEQ ID NO 27
<211> LENGTH: 23
<212> TYPE: DNA
<213> ORGANISM: Clostridium perfringens

<400> SEQUENCE: 27
agcagaccag taagactttc tac 23

<210> SEQ ID NO 28
<211> LENGTH: 21
<212> TYPE: DNA
<213> ORGANISM: Clostridium perfringens

<400> SEQUENCE: 28
agaacgtcca cagacaaact t 21

<210> SEQ ID NO 29
<211> LENGTH: 22
<212> TYPE: DNA

<213> ORGANISM: Clostridium botulinum

<400> SEQUENCE: 29
aacaggctcc tagattcagt ag                                    22

<210> SEQ ID NO 30
<211> LENGTH: 19
<212> TYPE: DNA
<213> ORGANISM: Clostridium botulinum

<400> SEQUENCE: 30
ccgagtgcag tttatcctt                                        19

<210> SEQ ID NO 31
<211> LENGTH: 23
<212> TYPE: DNA
<213> ORGANISM: Haemophilus influenzae

<400> SEQUENCE: 31
gacacgctaa acttaagcta gtt                                   23

<210> SEQ ID NO 32
<211> LENGTH: 17
<212> TYPE: DNA
<213> ORGANISM: Haemophilus influenzae

<400> SEQUENCE: 32
cctcaaacgg tggcttc                                          17

<210> SEQ ID NO 33
<211> LENGTH: 23
<212> TYPE: DNA
<213> ORGANISM: Enterococcus faecalis

<400> SEQUENCE: 33
gtcaactcat ttaaggattc act                                   23

<210> SEQ ID NO 34
<211> LENGTH: 24
<212> TYPE: DNA
<213> ORGANISM: Enterococcus faecalis

<400> SEQUENCE: 34
gatgttctct ttttcaactt acag                                  24

<210> SEQ ID NO 35
<211> LENGTH: 20
<212> TYPE: DNA
<213> ORGANISM: Enterococcus durans

<400> SEQUENCE: 35
tcaactcatt tgaggtttcg                                       20

<210> SEQ ID NO 36
<211> LENGTH: 25
<212> TYPE: DNA
<213> ORGANISM: Enterococcus durans

<400> SEQUENCE: 36
tgatgatctc ttttaaactt tacag                                 25

<210> SEQ ID NO 37
<211> LENGTH: 22
<212> TYPE: DNA

<213> ORGANISM: Enterococcus durans

<400> SEQUENCE: 37
aggcattctg tattgctagt ct                                    22

<210> SEQ ID NO 38
<211> LENGTH: 26
<212> TYPE: DNA
<213> ORGANISM: Streptococcus pyogenes

<400> SEQUENCE: 38
ttatgtcttc atttaacaaa ctaaag                                26

<210> SEQ ID NO 39
<211> LENGTH: 18
<212> TYPE: DNA
<213> ORGANISM: Streptococcus pyogenes

<400> SEQUENCE: 39
tcaagccatt agtttgcg                                         18

<210> SEQ ID NO 40
<211> LENGTH: 20
<212> TYPE: DNA
<213> ORGANISM: Streptococcus pyogenes

<400> SEQUENCE: 40
gacaatttcg taaccgtagc                                       20

<210> SEQ ID NO 41
<211> LENGTH: 25
<212> TYPE: DNA
<213> ORGANISM: Streptococcus agalactiae

<400> SEQUENCE: 41
gtattgattt aactaggtga tgaca                                 25

<210> SEQ ID NO 42
<211> LENGTH: 25
<212> TYPE: DNA
<213> ORGANISM: Streptococcus agalactiae

<400> SEQUENCE: 42
ttaactaact agacagtagc caaac                                 25

<210> SEQ ID NO 43
<211> LENGTH: 50
<212> TYPE: DNA
<213> ORGANISM: Escherichia coli

<400> SEQUENCE: 43
tcagtcttta cattcgcttg ccagctgcgg acggacacgc cactaacaaa      50

<210> SEQ ID NO 44
<211> LENGTH: 50
<212> TYPE: DNA
<213> ORGANISM: Staphylococcus aureus

<400> SEQUENCE: 44
cttcaaacgg cagtgtttag catatcctat taaggttgaa tcgcgttaac      50

<210> SEQ ID NO 45
<211> LENGTH: 50
<212> TYPE: DNA

<213> ORGANISM: Staphylococcus epidermidis

<400> SEQUENCE: 45
ccaacatgat actagcttga ttatatttca tctaaacaga cttcaagcgg                50

<210> SEQ ID NO 46
<211> LENGTH: 18
<212> TYPE: DNA
<213> ORGANISM: Escherichia coli

<400> SEQUENCE: 46
gcactggtcg tgggtttc                                                   18

<210> SEQ ID NO 47
<211> LENGTH: 24
<212> TYPE: DNA
<213> ORGANISM: Staphylococcus aureus

<400> SEQUENCE: 47
ttactctatc catatcgaaa gact                                            24

<210> SEQ ID NO 48
<211> LENGTH: 24
<212> TYPE: DNA
<213> ORGANISM: Staphylococcus epidermidis

<400> SEQUENCE: 48
ctattctaac catatccaat gact                                            24

<210> SEQ ID NO 49
<211> LENGTH: 50
<212> TYPE: DNA
<213> ORGANISM: Escherichia coli

<400> SEQUENCE: 49 cccccaggc gttacctggc accctgccct atggagcccg gactttcctc                 50

<210> SEQ ID NO 50
<211> LENGTH: 50
<212> TYPE: DNA
<213> ORGANISM: Staphylococcus aureus

<400> SEQUENCE: 50
taggatattt cattgccgtc aaattaatgc cttgatttat tgtttcatca                50

<210> SEQ ID NO 51
<211> LENGTH: 50
<212> TYPE: DNA
<213> ORGANISM: Staphylococcus epidermidis

<400> SEQUENCE: 51
taggttattt cattgccgtc aaattaatgc cttgatttat tgtttcatca                50

<210> SEQ ID NO 52
<211> LENGTH: 18
<212> TYPE: DNA
<213> ORGANISM: Escherichia coli

<400> SEQUENCE: 52
agtgtggctg gtcatcct                                                   18

<210> SEQ ID NO 53
<211> LENGTH: 50
<212> TYPE: DNA

```
<213> ORGANISM: Escherichia coli

<400> SEQUENCE: 53
ctcagaccag ctagggatcg tcgccttggt gagccgttac cccaccaaca          50

<210> SEQ ID NO 54
<211> LENGTH: 54
<212> TYPE: DNA
<213> ORGANISM: Escherichia coli

<400> SEQUENCE: 54
tccctagcct ccgctcttag gataaagact gactaagcat gtagtaccga ggat     54

<210> SEQ ID NO 55
<211> LENGTH: 55
<212> TYPE: DNA
<213> ORGANISM: Escherichia coli

<400> SEQUENCE: 55
tcctcggtac tacatgctta gtacattcaa cagaatccac accaacctcc tcata    55

<210> SEQ ID NO 56
<211> LENGTH: 48
<212> TYPE: DNA
<213> ORGANISM: Escherichia coli

<400> SEQUENCE: 56
cactacgact ctcggtctga ttctatttgc tcctaagagc ggaggcta            48

<210> SEQ ID NO 57
<211> LENGTH: 21
<212> TYPE: DNA
<213> ORGANISM: Escherichia coli

<400> SEQUENCE: 57
ctaagcatgt agtaccgagg a                                         21

<210> SEQ ID NO 58
<211> LENGTH: 18
<212> TYPE: DNA
<213> ORGANISM: Escherichia coli

<400> SEQUENCE: 58
tagcctccgc tcttagga                                             18

<210> SEQ ID NO 59
<211> LENGTH: 30
<212> TYPE: DNA
<213> ORGANISM: Escherichia coli

<400> SEQUENCE: 59
ttcaacagaa tccacaccaa cctcctcata                                30

<210> SEQ ID NO 60
<211> LENGTH: 66
<212> TYPE: DNA
<213> ORGANISM: Staphylococcus aureus

<400> SEQUENCE: 60
aagtctgttt agaagaaact taatcaaact agcatcatgt tggttgttta tcacttttca   60
tgatgc                                                          66

<210> SEQ ID NO 61
```

<211> LENGTH: 58
<212> TYPE: DNA
<213> ORGANISM: Staphylococcus aureus

<400> SEQUENCE: 61
ttgattaagt ttcttctaaa cagatacatc ataatcataa acttaactct gcaatcca    58

<210> SEQ ID NO 62
<211> LENGTH: 52
<212> TYPE: DNA
<213> ORGANISM: Staphylococcus aureus

<400> SEQUENCE: 62
cactacgact ctcggtctga ttctatttgc tcatgaaaag tgataaacaa cc    52

<210> SEQ ID NO 63
<211> LENGTH: 24
<212> TYPE: DNA
<213> ORGANISM: Staphylococcus aureus

<400> SEQUENCE: 63
tctgtttaga agaaacttaa tcaa    24

<210> SEQ ID NO 64
<211> LENGTH: 22
<212> TYPE: DNA
<213> ORGANISM: Staphylococcus aureus

<400> SEQUENCE: 64
ggttgtttat cacttttcat ga    22

<210> SEQ ID NO 65
<211> LENGTH: 30
<212> TYPE: DNA
<213> ORGANISM: Staphylococcus aureus

<400> SEQUENCE: 65
tcataatcat aaacttaact ctgcaatcca    30

<210> SEQ ID NO 66
<211> LENGTH: 65
<212> TYPE: DNA
<213> ORGANISM: Staphylococcus epidermidis

<400> SEQUENCE: 66
aacacatttc ggttaaatat aactgacagt atcatgttgg ttgtttattg cttagcatga    60
tgcga    65

<210> SEQ ID NO 67
<211> LENGTH: 57
<212> TYPE: DNA
<213> ORGANISM: Staphylococcus epidermidis

<400> SEQUENCE: 67
cagttatatt taaccgaaat gtgtacagaa agtgcaatga aatttgttga aaccttta    57

<210> SEQ ID NO 68
<211> LENGTH: 52
<212> TYPE: DNA
<213> ORGANISM: Staphylococcus epidermidis

<400> SEQUENCE: 68
cactacgact ctcggtctga ttctatttgc catcatgcta agcaataaac aa    52

```
<210> SEQ ID NO 69
<211> LENGTH: 24
<212> TYPE: DNA
<213> ORGANISM: Staphylococcus epidermidis

<400> SEQUENCE: 69
acacatttcg gttaaatata actg                                          24

<210> SEQ ID NO 70
<211> LENGTH: 23
<212> TYPE: DNA
<213> ORGANISM: Staphylococcus epidermidis

<400> SEQUENCE: 70
ttgtttattg cttagcatga tgc                                           23

<210> SEQ ID NO 71
<211> LENGTH: 30
<212> TYPE: DNA
<213> ORGANISM: Staphylococcus epidermidis

<400> SEQUENCE: 71
gaaagtgcaa tgaaatttgt tgaaaccttä                                    30

<210> SEQ ID NO 72
<211> LENGTH: 30
<212> TYPE: DNA
<213> ORGANISM: Escherichia coli

<400> SEQUENCE: 72
ttttaaaatt cctcggtact acatgcttag                                    30

<210> SEQ ID NO 73
<211> LENGTH: 33
<212> TYPE: DNA
<213> ORGANISM: Staphylococcus aureus

<400> SEQUENCE: 73
ttttaaaatt tgattaagtt tcttctaaac aga                                33

<210> SEQ ID NO 74
<211> LENGTH: 31
<212> TYPE: DNA
<213> ORGANISM: Staphylococcus epidermidis

<400> SEQUENCE: 74
ttttaaaatc atcatgctaa gcaataaaca a                                  31

<210> SEQ ID NO 75
<211> LENGTH: 27
<212> TYPE: DNA
<213> ORGANISM: Escherichia coli

<400> SEQUENCE: 75
ttttaaaatg cactggtcgt gggtttc                                       27

<210> SEQ ID NO 76
<211> LENGTH: 33
<212> TYPE: DNA
<213> ORGANISM: Staphylococcus aureus

<400> SEQUENCE: 76
ttttaaaatt tactctatcc atatcgaaag act                                33
```

<210> SEQ ID NO 77
<211> LENGTH: 33
<212> TYPE: DNA
<213> ORGANISM: Staphylococcus epidermidis

<400> SEQUENCE: 77
ttttaaaatc tattctaacc atatccaatg act                          33

<210> SEQ ID NO 78
<211> LENGTH: 27
<212> TYPE: DNA
<213> ORGANISM: Escherichia coli

<400> SEQUENCE: 78
ttttaaaata gtgtggctgg tcatcct                                 27

<210> SEQ ID NO 79
<211> LENGTH: 33
<212> TYPE: DNA
<213> ORGANISM: Trichomonas vaginalis

<400> SEQUENCE: 79
ttttaaaata tcctgaaaga cccgaagcct gtc                          33

<210> SEQ ID NO 80
<211> LENGTH: 41
<212> TYPE: DNA
<213> ORGANISM: Candida albicans

<400> SEQUENCE: 80
ttttaaaatt tgttcctcgt taaggtattt acattgtact c                 41

<210> SEQ ID NO 81
<211> LENGTH: 24
<212> TYPE: DNA
<213> ORGANISM: Trichomonas vaginalis

<400> SEQUENCE: 81
atcctgaaag acccgaagcc tgtc                                    24

<210> SEQ ID NO 82
<211> LENGTH: 32
<212> TYPE: DNA
<213> ORGANISM: Candida albicans

<400> SEQUENCE: 82
ttgttcctcg ttaaggtatt tacattgtac tc                           32

<210> SEQ ID NO 83
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
cccagggaga ccaaaagc                                           18

<210> SEQ ID NO 84
<211> LENGTH: 60
<212> TYPE: DNA
<213> ORGANISM: Escherichia coli

<400> SEQUENCE: 84

```
cgtgaagata tggctgccct tgagaaggat tatgaggagg ttggtgtgga ttctgttgaa      60

<210> SEQ ID NO 85
<211> LENGTH: 60
<212> TYPE: DNA
<213> ORGANISM: Staphylococcus aureus

<400> SEQUENCE: 85
atgttttcct tgttccctcc catgcctagc tggattgcag agttaagttt atgattatga      60

<210> SEQ ID NO 86
<211> LENGTH: 70
<212> TYPE: DNA
<213> ORGANISM: Staphylococcus epidermidis

<400> SEQUENCE: 86
tggtcctgcg cttgaggggg ggtgtctaag tttcccctttt aaggtttca acaaatttca     60 ttgcactttc                                                            70

<210> SEQ ID NO 87
<211> LENGTH: 9
<212> TYPE: DNA
<213> ORGANISM: Artificial Sequence
<220> FEATURE:
<223> OTHER INFORMATION: Description of Artificial Sequence: Synthetic
      immobilization sequence

<400> SEQUENCE: 87 ttttaaaat                                                              9
```

METHOD FOR RAPID IDENTIFICATION OF MICROORGANISMS

CROSS REFERENCE TO RELATED APPLICATIONS

This application is a continuation of U.S. patent application Ser. No. 11/197,594, filed Aug. 5, 2005, which claims priority to U.S. Provisional Application Ser. No. 60/599,858, filed Aug. 10, 2004, the disclosures of which are hereby incorporated herein by reference.

FIELD OF THE INVENTION

The present invention relates, in general, to probes, methods, and kits used to determine the presence or absence of a microorganism in a sample. The probes, methods, and kits comprise at least one capture probe and/or at least one detector probe.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Bacteremia and fungemia are life-threatening infections that require timely administration of appropriate antimicrobial therapy to prevent significant mortality. The term "septicemia" is used to describe the presence of organisms within the blood in association with laboratory and/or clinical findings that are indicative of infection such as fever, chills, malaise, tachycardia, hyperventilation, shock and leucocytosis. Weinstein et al. (*Rev. Infect. Dis.* 5: 54-70 (1983)) determined that the overall rate of mortality was 42% among 500 episodes of bacteremia and fungemia, with approximately half of the deaths attributable directly to septicemia. It has long been recognized, however, that the majority of bacteremias and fungemias are associated with the recovery of very low numbers of organisms from the blood. Indeed, it is not uncommon for less than 1 organism/mL of blood to be present, particularly after the initiation of antimicrobial therapy. The severity of such infections and the diverse spectrum of potential pathogens, therefore, necessitate highly sensitive methods of diagnosis that are capable of identifying a broad spectrum of bacteria and fungi. Classically, diagnosis is achieved through the use of broad-based culture methods that are amenable to the growth of a wide variety of pathogens from low-level inocula. Following growth and isolation in pure culture, the organisms are identified through the application of a battery of biochemical tests. Antimicrobial susceptibility testing is then conducted to permit modification of empirical therapy to an efficacious pathogen-specific regimen that minimizes cost and toxicity. There remains, however, a need to reduce the time between collection of specimens from a patient and administration of targeted antimicrobial therapy to provide an opportunity to reduce morbidity and mortality, defray the cost of therapy and hospitalization, and minimize the spread of antimicrobial drug resistance caused by ineffective or inappropriate therapy.

SUMMARY OF THE INVENTION

The present invention relates to a method for identifying the presence of at least one microorganism in a sample, the method comprising: (a) releasing RNA or DNA from the at least one microorganism in the sample; (b) contacting the RNA or DNA with at least one capture probe capable of hybridizing to a first target sequence of the RNA or DNA, wherein the contacting is performed under conditions that permit hybridization between the first target sequence and the at least one capture probe to form a microorganism-capture probe hybrid complex, and wherein the at least one capture probe comprises at least one sequence selected from the group consisting of SEQ ID NOs:1-53, 55, 56, 61, 62, 67, 68, and 72-78; and (c) detecting the presence of the microorganism-capture probe hybrid complex by (i) contacting the RNA or DNA with at least one detector probe capable of hybridizing to a second target sequence of the RNA or DNA, wherein the detector probe comprises at least one reporter group and wherein the contacting is performed under conditions that permit hybridization between the second target sequence and the at least one detector probe to form a microorganism-capture probe-detector probe hybrid complex, and wherein the at least one detector probe also comprises at least one sequence selected from the group consisting of SEQ ID NOs: 1-53, 55, 56, 61, 62, 67, 68, and 72-78; (ii) detecting the microorganism-capture probe-detector probe hybrid complex by detecting the at least one reporter group, wherein the presence of the microorganism-capture probe-detector probe hybrid complex indicates the presence of the at least one microorganism. In another embodiment, the reporter group is selected from the group consisting of a radioactive isotope, an enzyme, a fluorescent molecule and an amplification sequence. In a further embodiment, the amplification sequence initiates an amplification reaction selected from the group consisting of strand displacement amplification (SDA), polymerase chain reaction (PCR), reverse transcriptase-strand displacement amplification (RT-SDA), reverse transcriptase-polymerase chain reaction (RT-PCR), nucleic acid sequence based amplification (NASBA), transcription-mediated amplification (TMA), rolling circle amplification and Qβ replicase amplification. In an additional embodiment, detection of the microorganism-capture probe-detector probe hybrid complex is accomplished via non-specifically labeling the hybrid complex.

In an additional aspect, the first target sequence and the second target sequence comprise the same sequence. In another aspect, the capture probe is immobilized on a solid support before hybridizing to the first target sequence. In yet another aspect, the microorganism-capture probe hybrid complex is immobilized on a solid support. In a further aspect, the microorganism-capture probe-detector probe hybrid complex is immobilized on a solid support. In another aspect, the solid support is selected from the group consisting of latex beads, agarose beads, paramagnetic beads, ferric oxide, microarray chips, filter paper, nitrocellulose filters, nylon membranes, glass slides and cellular membranes. In a further aspect, the solid support is a microarray chip. In an additional aspect, two or more capture probes are immobilized on a single spot of the solid support. In a further aspect, the method described above further comprises an immobilization probe that is capable of hybridizing to the capture probe to be immobilized onto the solid support.

The methods of the present invention additionally provide a method for identifying the species of one or more microorganisms in a sample, the method comprising: (a) releasing RNA or DNA from the at least one microorganism in the sample; (b) contacting the RNA or DNA with at least one species-specific capture probe capable of hybridizing to a first target sequence of the RNA or DNA, wherein the contacting is performed under conditions that permit hybridization between the first target sequence and the at least one species-specific capture probe to form a species-specific microorganism-capture probe hybrid complex, and wherein the at least one species-specific capture probe comprises at least one sequence selected from the group consisting of SEQ ID NOs: 1-53, 55, 56, 61, 62, 67, 68, and 72-78; and (c) detecting the presence of the species-specific microorganism-capture probe hybrid complex by (i) contacting the RNA or DNA with at least one detector probe capable of hybridizing to a second target sequence of the RNA or DNA, wherein the detector probe comprises at least one reporter group and wherein the contacting is performed under conditions that permit hybridization between the second target sequence and the at least one detector probe to form a species-specific microorganism-capture probe-detector probe hybrid complex, and wherein the at least one detector probe also comprises at least one sequence selected from the group consisting of SEQ ID NOs: 1-53, 55, 56, 61, 62, 67, 68, and 72-78; (ii) detecting the species-specific microorganism-capture probe-detector probe hybrid complex by detecting the at least one reporter group, wherein the presence of the species-specific microorganism-capture probe-detector probe hybrid complex indicates the presence of the at least one microorganism belonging to the species. In a further embodiment, the amplification sequence initiates an amplification reaction selected from the group consisting of strand displacement amplification (SDA), polymerase chain reaction (PCR), reverse transcriptase-strand displacement amplification (RT-SDA), reverse transcriptase-polymerase chain reaction (RT-PCR), nucleic acid sequence based amplification (NASBA), transcription-mediated amplification (TMA), rolling circle amplification and Qβ replicase amplification. In another embodiment, the reporter group is selected from the group consisting of a radioactive isotope, an enzyme, a fluorescent molecule and an amplification sequence. In an additional embodiment, detection of the microorganism-capture probe-detector probe hybrid complex is accomplished via non-specifically labeling the hybrid complex.

In an additional aspect, the first target sequence and the second target sequence comprise the same sequence. In another aspect, the species-specific capture probe is immobilized on a solid support before hybridizing to the first target sequence. In yet another aspect, the species-specific microorganism-capture probe hybrid complex is immobilized on a solid support. In a further aspect, the species-specific microorganism-capture probe-detector probe hybrid complex is immobilized on a solid support. In another aspect, the solid support is selected from the group consisting of latex beads, agarose beads, paramagnetic beads, ferric oxide, microarray chips, filter paper, nitrocellulose filters, nylon membranes, glass slides and cellular membranes. In a further aspect, the solid support is a microarray chip. In an additional aspect, two or more species-specific capture probes are immobilized on a single spot of the solid support. In a further aspect, the method described above further comprises an immobilization probe that is capable of hybridizing to the capture probe to be immobilized onto the solid support.

The present invention further provides a method of determining the efficacy of an antimicrobial patient therapy, comprising: (a) identifying the presence or absence of a microorganism in a first patient sample according to the method claim 1; (b) identifying the presence or absence of the microorganism in a second patient sample according to the method of claim 1; wherein the first patient sample and the second patient sample are taken sequentially over time, and wherein detection of the microbial nucleic acid in the first sample and subsequent failure to detect nucleic acid in the second sample indicates a successful response to therapy; and detection of the microbial nucleic acid in the second sample indicates the continued presence of viable organisms in the sample. In an additional embodiment, the reporter group is selected from the group consisting of a radioactive isotope, an enzyme, a fluorescent molecule and an amplification sequence. In another embodiment, the amplification sequence initiates an amplification reaction selected from the group consisting of strand displacement amplification (SDA), polymerase chain reaction (PCR), reverse transcriptase-strand displacement amplification (RT-SDA), reverse transcriptase-polymerase chain reaction (RT-PCR), nucleic acid sequence based amplification (NASBA), transcription-mediated amplification (TMA), rolling circle amplification, and Qβ replicase amplification. In a further embodiment, the solid support is selected from the group consisting of latex beads, agarose beads, paramagnetic beads, ferric oxide, microarray chips, filter paper, nitrocellulose filters, nylon membranes, glass slides and cellular membranes. In an additional embodiment, the solid support is a microarray chip. In another embodiment, two or more capture probes are immobilized on a single spot of the solid support. In an additional embodiment, the method further comprises an immobilization probe that is capable of hybridizing to the capture probe to be immobilized onto the solid support. In still another embodiment, detection of the microorganism-capture probe-detector probe hybrid complex is accomplished via non-specifically labeling the hybrid complex.

The present invention provides a kit for detecting the presence or absence of at least one microorganism in a sample, comprising: (a) a solid support; (b) at least one capture probe comprising at least one capture sequence capable of hybridizing to at least one target sequence of RNA and/or DNA from the microorganism to form a microorganism-capture probe hybrid complex; wherein the at least the detector probe also comprises at least one sequence selected from the group consisting of SEQ ID NOs:1-53, 55, 56, 61, 62, 67, 68, and 72-78; (c) at least one detector probe capable of hybridizing to a second sequence of the RNA or DNA, wherein the detector probe comprises at least one reporter group, and wherein the detector probe comprises at least one sequence selected from the group consisting of SEQ ID NOs:1-53, 55, 56, 61, 62, 67, 68, and 72-78; and (d) a vessel to collect, concentrate, amplify or isolate the RNA or DNA. In one aspect, the vessel is selected from the group consisting of evacuated blood collection tubes, eppendorf tubes and test tubes. In another aspect, the solid support is selected from the group consisting of latex beads, agarose beads, paramagnetic beads, ferric oxide, microarray chips, filter paper, nitrocellulose filters, nylon membranes, glass slides and cellular membranes.

The present invention further provides an oligonucleotide for use in detecting a microorganism selected from the group consisting of *Staphylococcus aureus, Escherichia coli, Staphylococcus epidermidis, Klebsiella pneumoniae, Enterococcus faecalis, Pseudomonas aeruginosa, Streptococcus pneumoniae, Streptococcus mutans, Streptococcus gordonii, Clostridium perfringens, Clostridium botulinum, Haemophilus influenzae, Enterococcus durans, Streptococcus pyogenes, Streptococcus agalacticae, Clostridium difficile* and *Enterococcus faecium*. In one embodiment, *Staphylococcus aureus* is selected from the group consisting of SEQ ID NOs: 1, 2, 44, 47, 50, 61, 62, 73 and 76. In another embodiment, *Escherichia coli* is selected from the group consisting of SEQ ID NOs:3-7, 43, 46, 49, 52, 53, 55, 56, 72, 75 and 78. In a further embodiment, *Staphylococcus epidermidis* is selected from the group consisting of SEQ ID NOs:8-10, 45, 48, 51, 67, 68, 74 and 77. In an additional embodiment, *Klebsiella*

*pneumoniae* is selected from the group consisting of SEQ ID NOs:11-13. In yet another embodiment, *Enterococcus faecalis* is selected from the group consisting of SEQ ID NOs:14-16. In one aspect, *Pseudomonas aeruginosa* is selected from the group consisting of SEQ ID NOs:17 and 18. In another aspect, *Streptococcus pneumoniae* is selected from the group consisting of SEQ ID NOs:19 and 20. In a further aspect, *Streptococcus mutans* is selected from the group consisting of SEQ ID NOs:21 and 22. In an additional aspect, *Streptococcus gordonii* is selected from the group consisting of SEQ ID NOs:23 and 24. In yet another aspect *Clostridium perfringens* is selected from the group consisting of SEQ ID NOs:27 and 28. In another embodiment, *Clostridium botulinum* is selected from the group consisting of SEQ ID NOs:29 and 30. In a further embodiment, *Haemophilus influenzae* is selected from the group consisting of SEQ ID NOs:31 and 32. In an additional embodiment, *Enterococcus durans* is selected from the group consisting of SEQ ID NOs:35-37. In yet another embodiment, *Streptococcus pyogenes* is selected from the group consisting of SEQ ID NOs:38-40. In a further aspect, *Streptococcus agalacticae* is selected from the group consisting of SEQ ID NOs:41 and 42. In another aspect, *Clostridium difficile* is selected from the group consisting of SEQ ID NOs:25 and 26. In an additional aspect, *Enterococcus faecium* is selected from the group consisting of SEQ ID NOs:33 and 34.

BRIEF DESCRIPTION OF THE DRAWINGS

FIGS. 5A-C depict exemplary capture probes according to the present invention immobilized to a different spots of an array using immobilization probes. Target oligonucleotides are bound to the capture probes, and detector probes are bound to the target oligonucleotides.

FIG. 6 depicts synthetic target sequences derived from discontiguous regions within the ssrA (small stable RNA A) genes of *E. coli, S. aureus*, and *S. epidermidis*. Capture probes and detector probes that may be used to capture and detect these sequences are also shown.

FIGS. 7A-E depict results from exemplary assays using methods described herein using probes according to the invention.

FIG. 7F depicts the arrangement of immobilization probes and controls on chips according to the invention.

FIG. 8A depicts the arrangement on chips of capture probes according to the invention and controls used in exemplary assays using methods described.

FIGS. 8B-E depict results from exemplary assays using methods described herein using probes according to the invention.

DETAILED DESCRIPTION OF THE INVENTION

Figure 1:
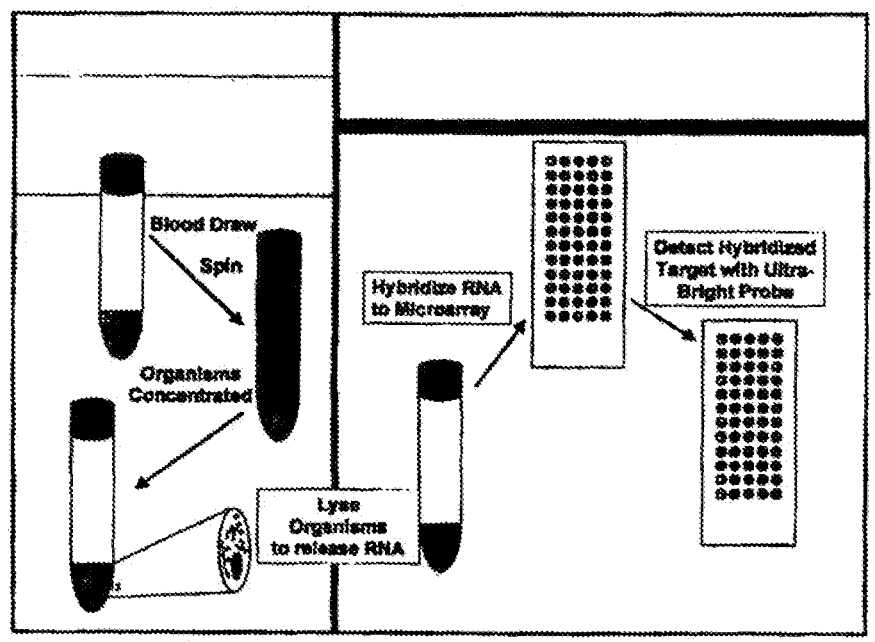
FIG. 1 depicts one embodiment of the use of the probes and methods of the present invention.

The present invention relates to probes, methods, and kits for identifying the presence or absence of at least one microorganism in a sample. The probes of the present invention comprise single-stranded nucleic acid or nucleic acid derivatives such as a peptide nucleic acid. Probes of the present invention comprise (a) nucleic acid sequences capable of hybridizing to nucleic acid sequences specific to microorganisms and/or (b) nucleic acid sequences capable of hybridizing to another probe according to the present invention.

Probes capable of binding microorganism RNA and/or DNA are referred to herein as "capture probes" and/or "detector probes." Capture probes are often, but need not be, immobilized to a solid support. Detector probes often, but need not, comprise a means for facilitating detection of the microorganism RNA and/or DNA. For example, detector probes often, but need not, comprise a reporter group. Methods of the present invention comprise releasing RNA and/or DNA from at least one microorganism in a sample and contacting the RNA and/or DNA with at least one capture probe under conditions that permit specific hybridization between the microorganism RNA and/or DNA and at least a portion of the probe to form a hybrid complex. A hybrid complex between a capture probe and microorganism RNA and/or DNA may be referred to herein as a "microorganism-capture probe hybrid complex." The microorganism-capture probe hybrid complex may, but need not, be detected with a detector probe that likewise forms a specific hybrid with the microorganism RNA and/or DNA. A hybrid complex between a detector probe and microorganism RNA and/or DNA that is also hybridized to a capture probe may be referred to herein as a "microorganism-capture probe-detector probe hybrid complex." The presence or absence of a specific hybrid complex correlates with the presence or absence of the microorganism.

The probes and/or identification methods of the present invention may be used to identify the genus and/or species of one or more microorganisms. The probes and/or identification methods of the present invention may be used to determine whether one or more microorganisms of a particular genus and/or species is present in a sample. Alternatively, the probes and/or identification methods of the present invention may be used to identify whether a sample contains one or more microorganisms belonging to a general classification category such as a taxonomic family, or to even a broader category. As a non-limiting example, the probes and/or methods of the present invention can be used to determine whether a sample contains a fungus, bacterium, virus, or parasitic microorganism. The probes and/or methods of the present invention may also be used to determine susceptibility to antimicrobial agents by determining the presence, absence and/or expression of specific markers, such as the antimicrobial drug resistance genes mecA, vanA or vanB.

For the purposes of the present invention, the term "microorganism" is used to mean a prokaryotic organism, a bacterium, a fungus, a parasite, a protozoan, or a virus. These terms are not mutually exclusive; as two non-limiting examples, many protozoa are parasites, and all bacteria are prokaryotic organisms. A "sample," as the term is used herein, can be derived from an animal and can include, for example, blood, urine or other body fluids, organs, tissues and any portions thereof, or can be obtained from the environment, such as air, water or soil, or from material intended for human or animal use or consumption, such as meat, fish or dairy produce, and even cosmetics. Furthermore, the methods of the present invention may be performed on the entire sample or only a portion or fraction thereof. As a non-limiting example, a sample may be whole blood from a subject, or the sample may be a collection of platelets isolated or concentrated from a subject's blood. As used herein, "subject" means an animal. The term "animal" includes, but is not limited to, birds, fish, and mammals, such as but not limited to, human and non-human primates, farm animals, and companion animals. As used herein, the terms "subject" and "patient" are used interchangeably. The sample can also be derived from in vitro cultures of cells. The cells of the cell culture can be eukaryotic or prokaryotic including, but not limited to, animal cells, plant cells, and bacterial cells. The cell cultures can be, for example, derived cells isolated from tissues, organs, or body fluid of an animal or plant. In some embodiments, the biological sample comprises animal cells that are derived from a subject. The term "sample" also encompasses a culture medium that has been inoculated with a sample taken from a mammal, food, the environment, cosmetics, or the like to permit any microorganisms present in the sample to replicate to detectable levels.

In certain embodiments, a sample is treated to concentrate or isolate microorganisms before releasing nucleic acid from them. Microorganisms may be concentrated in a sample prior to, or simultaneously with, the release of the nucleic acids. Alternatively, the DNA and/or RNA may be released prior to the concentration process.

Figure 4:
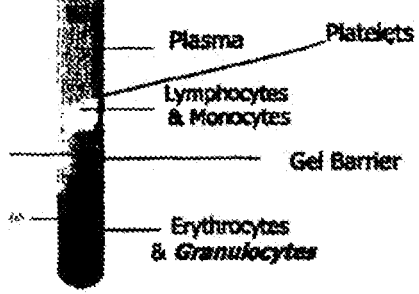
FIG. 4 depicts a vessel capable of concentrating the microorganisms in a sample, such as blood, that can be used in the methods and kits of the present invention.

Many methods for concentrating and/or isolating microorganisms are known in the art. Examples of ways to concentrate the microorganisms in the biological sample include, but are not limited to, using a Wampole Isolator™ tube (Wampole Laboratories, New Jersey, USA), a BD CPT™ tube (Becton, Dickinson and Company, New Jersey, USA), di-electrophoresis, traveling wave field migration, and electrophoresis. For example, FIG. 1 illustrates one embodiment of the methods of the present invention in which bacteria in blood are concentrated into a volume of 300 µL using a Wampole isolator tube. As another example, FIG. 4 depicts a vessel capable of concentrating the microorganisms in a sample, such as blood, that can be used in the methods and kits of the present invention. In some embodiments, a sample is treated to differentially separate microorganisms. In such embodiments, separate samples containing different microorganisms may be obtained. Examples 1-3 hereinbelow demonstrate differential separation of microorganisms using density gradients and matrices.

As the present invention contemplates, concentration of microorganisms and/or their nucleic acids can be accomplished in any number of steps including, but not limited to, one, two or three steps, where, in each step, the sample is progressively more concentrated. As a non-limiting example, microorganisms or their nucleic acids may be first concentrated using, for instance, a Wampole Isolator™ tube. To continue this example, the concentrated sample then may be concentrated further, separating intact microorganisms or their nucleic acids using, for instance, electrophoresis.

As used herein, the terms "nucleic acids" and "oligonucleotides" are used to mean DNA or RNA, as is recognized in the art. Nucleic acids may be single-stranded or double-stranded. Nucleic acids may be "released" from a microorganism using any means that will allow a capture probe access to hybridize the DNA or RNA. Hence, a "released" nucleic acid is a nucleic acid that is in a physical and chemical environment that allows nucleic acid probes to bind to it. Additionally, both DNA and RNA may be released by the same processes. Examples of ways that DNA or RNA may be released include, but are not limited to, lysing the microorganisms using, for example, heat, enzymes, detergents, buffers, acids, bases, chaotropes, physical shearing in the presence of beads or particles and the application of pressure. As is contemplated by the present invention, the act of collecting, isolating, or concentrating the sample, or the portion thereof to be tested, may sufficiently release the nucleic acids that are subject to capturing. For the purposes of the present invention, the DNA or RNA to be used may be, but need not be, purified, isolated or concentrated further after release. Methods for purification, isolation, and concentration of nucleic acids are well-known in the art. It is preferable that nucleic acids released from microorganisms be in single-stranded form and lack internal secondary structure before they are contacted with probe(s) according to the present invention. Accordingly, the methods of the present invention may also include one or more denaturing step, to denature any double-stranded nucleic acids or nucleic acids that possess internal secondary structure that are released from the microorganisms, prior to contacting the DNA or RNA with the capture probe. However, such a denaturing step is not required, particularly where the acts of releasing, purifying, isolating, and/or concentrating the nucleic acids also result in their denaturation. Methods for denaturation of nucleic acids are well-known in the art.

Microorganisms that are to be detected may be referred to as "target microorganisms." Nucleic acids released by microorganisms that are to be detected may be referred to as "target nucleic acids" or "target oligonucleotides." Target oligonucleotides will usually comprise at least one sequence that is capable of binding to a capture probe and/or a detector probe being used to detect microorganisms in a sample. Such a sequence may be referred to herein as a "target sequence."

Once nucleic acids are released from the microorganisms, they may be contacted with one or more capture probes that are immobilized on a solid support. As an alternative, the released nucleic acids may be contacted with a free (non-immobilized) capture probe to form a hybrid complex, which is then contacted with a solid support that immobilizes the hybrid complex. As yet another alternative, capture probes may remain free (i.e., not immobilized). In such cases, hybrid complexes may be isolated by art-known means such as electrophoresis.

As used herein, a "capture probe" is a nucleic acid, or nucleic acid derivative such as a peptide nucleic acid, that is capable of binding to a released nucleic acid. A capture probe contains at least one single-stranded portion, or sequence, that is capable of contacting and hybridizing with released microorganism nucleic acids. A sequence that is capable of contacting and hybridizing with released microorganism nucleic acids may be referred to herein as a "capture sequence." As used herein, capture probes may be classified by, for example, the microorganism(s) to which their capture sequence(s) is capable of binding. Thus, capture probes of the same "type" comprise capture sequence(s) capable of binding to the same microorganism(s). A capture probe comprises at least one capture sequence. A capture probe often also comprises, but is not required to comprise, sequences in addition to at least one capture sequence. Such additional sequences may, for example, facilitate immobilization of the capture probe.

Detector probes may be used to facilitate the detection of nucleic acids that have been released from microorganisms. Nucleic acids that have been released from microorganisms may be contacted with one or more detector probes. As used herein, a "detector probe" is a nucleic acid, or nucleic acid derivative such as a peptide nucleic acid, that is capable of binding to a released nucleic acid and that is capable of being detected, thereby facilitating detection of the released nucleic acid. A detector probe contains at least one single-stranded portion, or sequence, that is capable of contacting and hybridizing with a released microorganism nucleic acid. As with capture probes, a sequence of a detector probe that is capable of contacting and hybridizing with released microorganism nucleic acids may be referred to herein as a "capture sequence." A detector probe is preferably bound to a reporter group to facilitate detection. A detector probe to can be bound to a reporter group before or after the detector probe is hybridized to a target oligonucleotide. Reporter groups are known in the art and are discussed in more detail hereinbelow.

The capture sequence of a detector probe will usually hybridize to a different target sequence of a target oligonucleotide than the target sequence to which the capture sequence of the capture probe hybridizes. Accordingly, a target oligonucleotide can be bound and detected by a detector probe while is bound to a capture probe. In such embodiments, either the capture probe or the detector probe may be hybridized to the target oligonucleotide first. In certain embodiments it may be desirable to utilize a capture probe and detector probe each having a capture sequence that binds to the same target sequence. In such embodiments, a target oligonucleotide may be captured by a capture probe, the capture probe-target complex may be isolated, the capture probe-target complex may be denatured, and the detector probe may them be hybridized to the target oligonucleotide.

As with capture probes, detector probes may be classified by, for example, the microorganism(s) to which their capture sequence(s) is capable of binding. Thus, detector probes of the same "type" comprise capture sequence(s) capable of binding to the same microorganism(s). A detector probe comprises at least one capture sequence. A detector probe often also comprises, but is not required to comprise, sequences in addition to at least one capture sequence. Such additional sequences may, for example, facilitate the binding of the detector probe to a reporter group.

In some embodiments, capture probes and/or detector probes comprise linker molecules such as, but not limited to, carbon chains or nucleic acid sequences that are not complementary to the target oligonucleotide. A linker molecule may serve, for example, to attach a probe to a solid surface, to bind a probe to another type of molecule (such as, for example, a protein), to attach a probe to a reporter group, or to bind a probe to another probe. A sequence that serves to immobilize a capture probe to a solid surface may be referred to herein as an "immobilization sequence." A probe comprising an immobilization sequence may be referred to herein as an "immobilization probe." Such non-complementary linkages may reduce steric hindrance and may also improve the kinetics of hybridization by increasing the accessibility of the probes, particularly the capture sequence(s), to the bulk solution. Examples of nucleic acid sequences that may be used as linker molecules include the human genes K-alpha (tubulin alpha-1), PPIA (peptidylprolyl isomerase A), and UBC (ubiquitin-conjugating enzyme E2A), and portions thereof. FIGS. 5A-C provide non-limiting illustrations of capture probes according to the present invention immobilized to an array using linkers comprising portions of K-alpha, PPIA, and UBC.

Capture probes of the current invention may be "immobilized" onto a solid support. As used herein, "immobilized" means affixed to a solid support such that movement of the capture probe in a solution is limited, i.e., a capture probe that is immobilized on a solid support will not dissociate from the solid support unless it is subjected to a condition or procedure that would cause it to dissociate.

Figure 3:
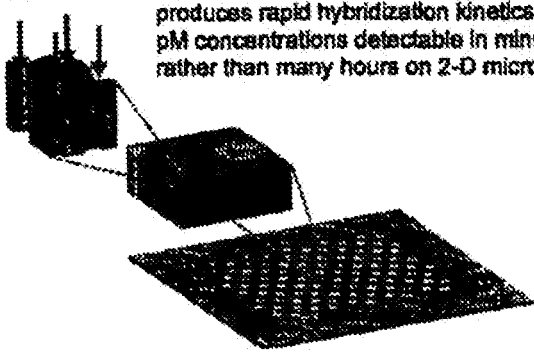
FIG. 3 depicts an example of a solid support that may be used to immobilize probes of the present invention and may be used in the methods and kits of the present invention.

As used herein, a "solid support" is a structure or a scaffold that will not dissolve in a liquid or gas solution. Examples of solid supports include, but are not limited to, latex beads, agarose beads, sepharose beads, paramagnetic beads, ferric oxide, microarray chips, filter paper, nitrocellulose filters, nylon membranes, vessels, glass slides, and even cellular membranes. In some embodiments, the method of the present invention utilizes a three-dimensional microarray, such as, for example, the MetriGenix® Flow-Thru Chip® (MetriGenix, Inc., Maryland, USA), which facilitates increased hybridization kinetics. An example of a MetriGenix® Flow-Thru Chip® is illustrated in FIG. 3. Such porous arrays offer increased surface area for attachment of probes over conventional two-dimensional chips and permit the flow of liquid back and forth over the chip surface of the array, thereby increasing the opportunity for contact between the capture probe and target sequence. In some embodiments, each spot on an array may correspond to, as non-limiting examples, a different species of microorganisms, group of microorganisms or epidemiological marker. In other embodiments, different types of capture probes may be immobilized on the same spot of an array. Multiple spots for each analyte or group of analytes may also be present.

Capture probes may be immobilized onto solid supports using any of the many art-known methods. Preferably, the immobilization does not adversely affect the capture probe's ability to bind to microorganism DNA and/or RNA or to other probes. A capture probe may be immobilized directly to the solid support, or it may be immobilized indirectly via attachment to another molecule that is immobilized on the solid support. For example, a capture probe may be immobilized using chemical or linker moieties such as carbon chains or polyethylene glycol (PEG). In such cases, the binding of the capture probe may be non-specific. Alternatively, methods of using chemical moieties to bind specific nucleic acid sequences are known and may be used with the present invention. As a non-limiting example, capture probes may be biotinylated, with biotin possessing the ability to bind to avidin or streptavidin. Continuing the example, the solid support may have avidin or streptavidin bound to it. Such a scheme is a non-limiting example of a method for immobilizing capture probes without adversely affecting their ability to bind microorganism DNA and/or RNA because the biotin can be located at the opposite end of the molecule from the sequence capable of binding microorganism DNA and/or RNA (which may be called a "capture sequence"), or the biotin may be located on an internal branch of the capture probe that will result in its being located at a sufficient distance from the capture sequence that the binding of the capture sequence to microorganism DNA and/or RNA is not hindered.

Figure 2A:
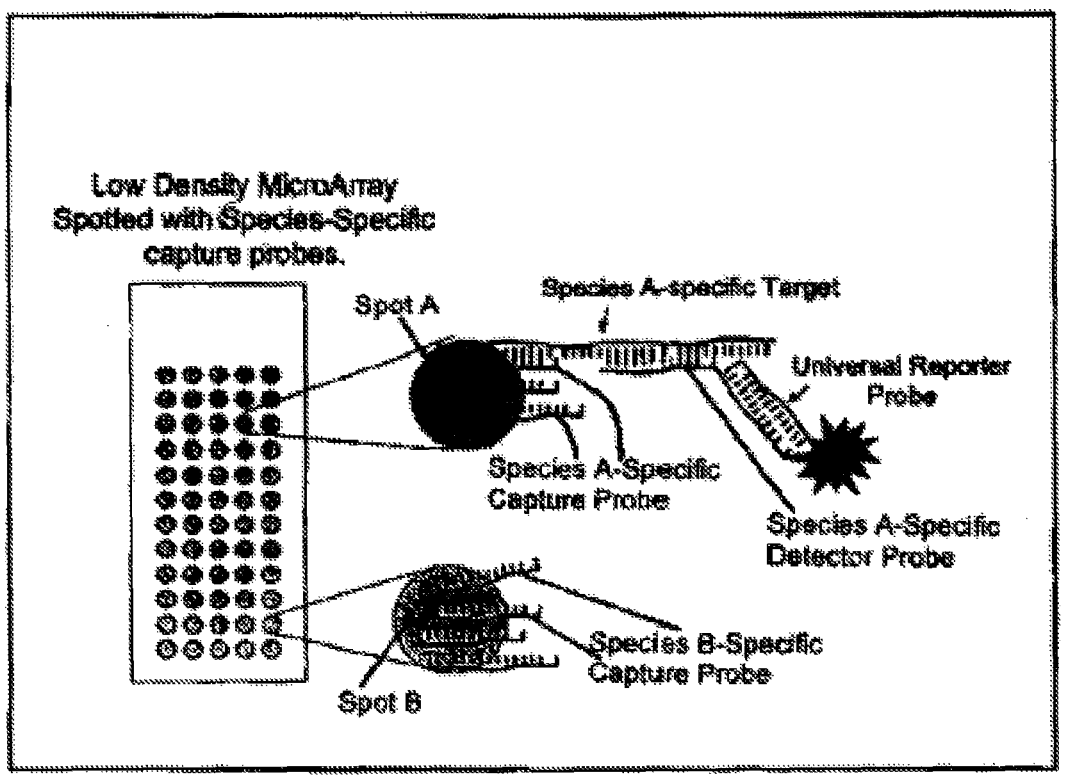
FIG. 2A depicts detection of a target oligonucleotide using species-specific capture probes directly immobilized to a solid support.
Figure 2B:
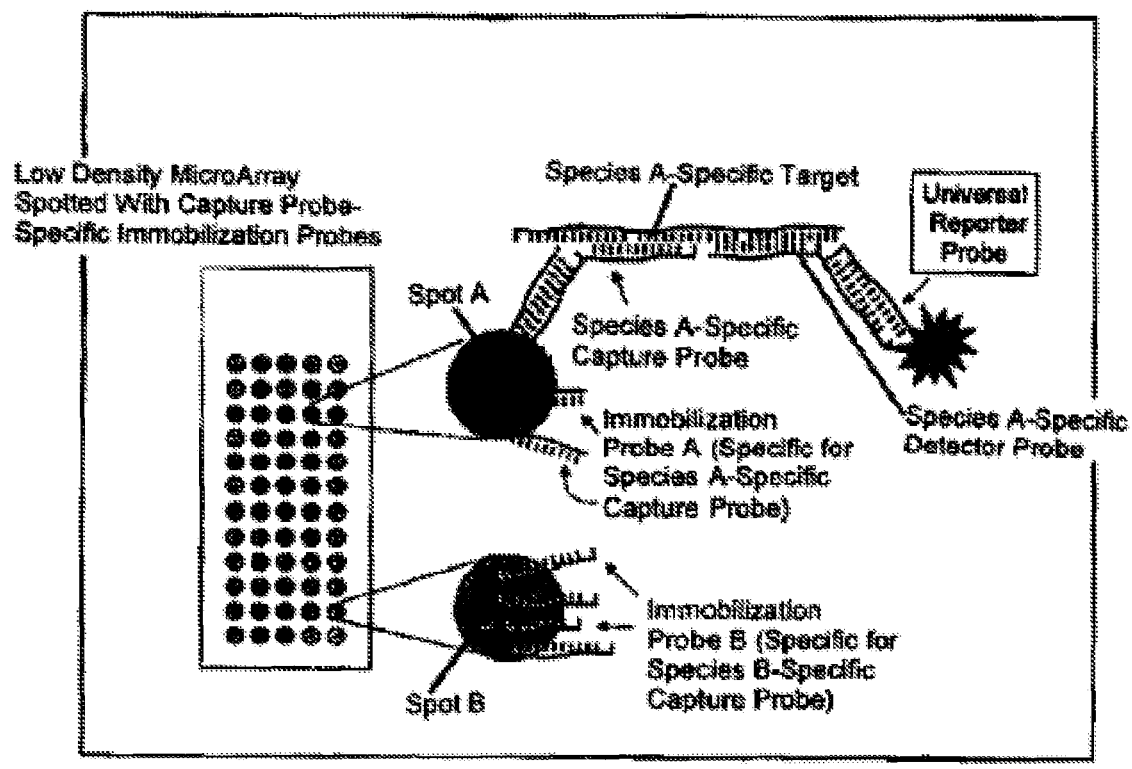
FIG. 2B depicts detection of a target oligonucleotide using species-specific capture probes immobilized to a solid support via immobilization probes.

As another example, capture probes may also be immobilized using another single-stranded oligonucleotide probe that is itself immobilized and that is capable of hybridizing with the capture probe to be immobilized. Such oligonucleotide probes may be called "immobilization probes." The use of immobilization probes is another non-limiting example of a method for immobilizing capture probes without adversely affecting their ability to bind microorganism DNA and/or RNA because the sequence on the capture probe that is capable of binding to the immobilization probe (which may be called an "immobilization sequence") can be located at the opposite end of the molecule from the sequence capable of binding microorganism DNA and/or RNA (which may be called a "capture sequence"), or the immobilization sequence may be located on an internal branch of the capture probe that will result in its being located at a sufficient distance from the capture sequence that the binding of the capture sequence to microorganism DNA and/or RNA is not hindered. An example of immobilization of a capture probe via an immobilization probe is illustrated in FIG. 2B. Examples of nucleic acid sequences that may be used as immobilization probes include the human genes K-alpha (tubulin alpha-1), PPIA (peptidylprolyl isomerase A), and UBC (ubiquitin-conjugating enzyme E2A). (FIGS. 5A-C). In an alternative embodiment, immobilization probes may comprise non-specific sequences such as poly-A or poly-T oligomers. In a further embodiment they may also comprise random sequences of nucleotides or nucleotide homologues with no homology or complementarity to naturally occurring nucleic acid sequences.

In some embodiments, capture probes may be immobilized directly or indirectly on a solid support in a pattern of discrete areas, or "spots." Such a pattern, or a solid support capable of supporting such a pattern, may be referred to herein as an "array," a "microarray," or a "chip." The immobilization of probes of different types to a single microarray or chip facilitates the simultaneous determination of whether different microorganisms are present in a single sample.

In certain embodiments, only a single type of capture probe is immobilized to any one spot, and different types of capture probes may be immobilized to different spots. In such embodiments, the identity of the capture probe immobilized in any given spot is known, so microorganisms hybridized to capture probes in different spots can be identified and differentiated from one another by means of their locations. Examples of immobilization of different types of capture probes in different spots of arrays are illustrated in FIGS. 2A and 2B and in FIGS. 5A-C.

FIGS. 5A-C provide non-limiting exemplary illustrations of different types of capture probes according to the present invention immobilized to different spots of an array using immobilization probes and immobilization sequences. Immobilization probes comprising approximately 60 nucleotides in length to the human genes K-alpha (tubulin alpha-1) (FIG. 5A), PPIA (peptidylprolyl isomerase A) (FIG. 5B), or UBC (ubiquitin-conjugating enzyme E2A) (FIG. 5C) are immobilized to an array. Each of the immobilization probes is hybridized to a capture probe comprising approximately 30 bases of sequence complementary to K-alpha (FIG. 5A), PPIA (FIG. 5B), or UBC (ubiquitin-conjugating enzyme E2A) (FIG. 5C) 3' to a capture sequence specific for *E. coli* (FIG. 5A), *S. aureus* (FIG. 5B), or *S epidermis* (FIG. 5C).

In other embodiments, more than one type of capture probe is immobilized in a single spot. In such embodiments, it will often be useful to use employ detector probes such that each detector probe of the same type is bound to a reporter group that is differentiable from reporter groups bound to any other type of detector probe. As a non-limiting example, one could perform an assay in which detector probes that bind to a target sequence from *E. coli* are labeled with fluorescein, and detector probes that bind to a target sequence from *S. aureus* are labeled with rhodamine. In such an assay, the presence of *E. coli* could be differentiated from the presence of *S. aureus* by the difference in the colors of the fluorescent labels. Of course, detector probes with differentiable labels may also be used in conjunction with the immobilization of different types of capture probes in different spots, thereby facilitating the performance of complex assays.

Detector probes may be attached directly or indirectly to a reporter group. As an example of an indirect attachment using a linker molecule, a detector probe may comprise a "reporter adapter sequence" linker. A reporter adapter sequence is a portion of a detector probe that is capable of binding via hybridization to a single-stranded oligonucleotide that bears a reporter group, which may be referred to herein as a "reporter probe." FIGS. 2A-B provide exemplary illustrations of a capture probe hybridized to a target oligonucleotide, which is in turn hybridized to a detector probe. The detector probe is hybridized to a reporter probe. In certain embodiments, detector probes of different types may comprise the same reporter adapter sequence, thereby facilitating the detection of different microorganisms using a single reporter probe, which may be referred to herein as a "universal reporter probe." Such an embodiment is illustrated in FIGS. 2A and B. In other embodiments, detector probes of different types may comprise different reporter adapter sequences, thereby facilitating the use of differentiable reporter probes to detect different microorganisms.

Capture probes and detector probes may be "protected" from prematurely hybridizing to random nucleic acids by having a protecting group situated on or near the capture or detector probe. As non-limiting examples, protecting groups include single-stranded nucleic acid that is partially complementary to the capture probe to be protected, or an antibody or a binding fragment thereof that binds to the single-stranded portion of the capture or detector probe to be protected.

Hybridization between a microorganism nucleic acid and a capture probe or detector probe may be referred to herein as a "hybridization event." A hybridization event will form a "hybrid complex." As used herein, a "hybrid complex" is a double-stranded nucleic acid comprising at least a portion of a capture probe or detector probe (usually a capture sequence) and at least a portion of a target oligonucleotide (usually a target sequence). A hybrid complex need not be double-stranded along its entire length. Furthermore, for the purposes of the present invention, a capture probe or detector probe and a target oligonucleotide need not have a complementary base pairing at every base for a hybridization event to occur. Further still, for the purposes of the present invention, a capture sequence and a target sequence need not have a complementary base pairing at every base for a hybridization event to occur. In other words, the present invention contemplates that a hybrid complex will be formed even if a target oligonucleotide hybridizes to a capture or detector probe such that a portion of the capture or detector probe or target nucleic acid is single-stranded after hybridization because the target oligonucleotide did not hybridize to the entire length of the capture or detector probe. In some embodiments of the present invention, a portion of a capture or detector probe remains single-stranded after hybridization to a target oligonucleotide. In some other embodiments, a portion of a target oligonucleotide remains single-stranded after hybridization to a capture or detector probe. In still other embodiments, portion(s) of each of a target oligonucleotide and a capture or detector probe remain(s) single-stranded after hybridization to one another. A "portion" can be one or more nucleic acids in length. Such single-stranded portions may occur within and/or outside of a capture sequence and/or a target sequence. Single-stranded portions within a capture sequence and/or target sequence may occur, as a non-limiting example, because the capture sequence and the target sequence are not 100% complementary. Single-stranded portions outside of a capture sequence and/or target sequence may occur, as a non-limiting example, because the capture and/or detector probe contains portions that are not intended to bind to the target oligonucleotide. Single-stranded portions outside of a capture sequence and/or target sequence may occur, as another non-limiting example, because the target oligonucleotide comprises sequences in addition to the target sequence. For example, a capture probe will often (but need not) comprise a sequence used to immobilize it to a solid support. As another example, a detector probe will often (but need not) comprise a sequence used to bind it to a reporter group. As yet another example, a target oligonucleotide will often (but need not) comprise sequences 3' and/or 5' to the target sequence(s).

A solid support may have immobilized to or on it one or various combinations of probes that are microorganism-specific, probes that are for epidemiological markers (e.g., IS6110-based probes used for *Mycobacterium tuberculosis*), and/or probes that are for drug resistance markers (e.g., mecA-based probes for methicillin resistance in *S. aureus* or rpoB-based probes for detection of rifampin resistance in *M. tuberculosis*). As used herein, the term "microorganism-specific probe" includes probes that are capable of hybridizing with a target sequence derived or released from a single microorganism species. Such probes may also be referred to herein as "species-specific probes." The term "microorganism-specific probe" also includes probes that are capable of hybridizing with target sequences from more than one species of microorganism from a single genus of microorganism (e.g., IS6110 for the detection of the *M. tuberculosis* complex (*M. tuberculosis, M. bovis, M. microti,* and *M. africanum*); probes based on conserved regions of the 16S rRNA, 18S rRNA, RNase P or ssrA gene sequences). For example, a microorganism-specific probe may be designed to form a hybrid with nucleic acid sequences from both *S. aureus* and *S. epidermidis*, but not with *E. coli*. Such probes may also be referred to herein as "genus-specific probes." In some embodiments, a genus-specific probe will hybridize to sequences derived from all or many of the microorganisms belonging to the same genus of classification. As used herein, a "multi-genus probe" will hybridize to nucleic acid from microorganisms belonging to two or more different genera. A probe may hybridize to an antimicrobial resistance marker that may be present in one or more species, for example. Such a probe may be species-specific, genus-specific, or multi-genus, depending on how widely the antimicrobial resistance marker is distributed through phylogeny. Whether a microorganism-specific probe, as contemplated by the present invention, hybridizes to a target sequence derived or released from a single microorganism species, to target sequences derived or released from more than one microorganism species within the same genus of microorganisms, or to target sequences derived or released from microorganisms from different genuses may also depend on the hybridization and wash conditions used in the assay.

As described above for capture probes, detector probes may be microorganism-specific probes, probes that are for epidemiological markers, and/or probes that are for drug resistance markers. Various combinations of capture probes and detector probes may be used to discriminate between organisms present in a sample. For instance, a genus-specific capture probe may be used to immobilize microorganisms of a selected genus, which then may be detected as a genus with one or more genus-specific detector probes, or which may be discriminated by species with one or more species-specific detector probes. More than one type of capture probe may be used concurrently in the methods of the present invention. Likewise, more than one type of detector probe may be used concurrently in the methods of the present invention.

As non-limiting examples, oligonucleotide probes comprising one or more of the sequences set forth in the following table (Table 1) are particularly useful for detecting and identifying bacteria of the indicated species. Oligonucleotide probes comprising one or more of the sequences set forth in Table 1 can be used as capture and/or detector probes to detect nucleic acids from the indicated bacterial species. Oligonucleotide probes comprising regions that are homologous to the oligonucleotide probes set forth in Table 1 are also useful for capturing and/or detecting the indicated species. In general, oligonucleotides containing sequences that are at least about 85%, at least about 90%, at least about 95%, or about 100% homologous to the oligonucleotides of Table 1 are useful.

The sequences in Table 1 can be used as species-specific capture and/or detector sequences to detect and/or differentiate between particular species of microorganisms. Sequences from Table 1 may, but need not, comprise portion(s) of longer oligonucleotides. For example, probes according to the invention may comprise one or more sequences from Table 1 and/or additional sequences.

TABLE 1

| SEQ ID NO: | Species | Reference Strain | Target Gene | Oligo Name | 5'-3' Sequence | Tm (° C.)* | Rank** |
|---|---|---|---|---|---|---|---|
| 1 | *Staphylococcus aureus* | NCTC 8325 | ssrA | S_aur-1 | TTG ATT AAG TTT CTT CTA AAC AGA | 58.9 | 1 |
| 2 | *Staphylococcus aureus* | NCTC 8325 | ssrA | S_aur-2 | TCA TGA AAA GTG ATA AAC AAC C | 59.7 | 1 |
| 3 | *Escherichia coli* | O157:H7 EDL933 | ssrA | E_coli-1 | AAT TCC TAC GTC CTC GGT A | 59.2 | 2 |
| 4 | *Escherichia coli* | O157:H7 EDL933 | ssrA | E_coli-2 | TAC ATT CGC TTG CCA GC | 60.0 | 2 |
| 5 | *Escherichia coli* | O157:H7 EDL933 | ssrA | E_coli-3 | CTA GCC TGA TTA AGT TTT AAC G | 59.6 | 2 |
| 6 | *Escherichia coli* | ATCC 133 | ssrA | E_coli-4 | TCC TCG GTA CTA CAT GCT TAG | 59.8 | 2 |

TABLE 1-continued

| SEQ ID NO: | Species | Reference Strain | Target Gene | Oligo Name | 5'-3' Sequence | Tm (° C.)* | Rank** |
|---|---|---|---|---|---|---|---|
| 7 | Escherichia coli | ATCC 133 | ssrA | E_coli-5 | TCC TAA GAG CGG AGG CTA | 60.3 | 2 |
| 8 | Staphylococcus epidermidis | SR1 | ssrA | S_epi-1 | CAT CAT GCT AAG CAA TAA ACA A | 61.4 | 3 |
| 9 | Staphylococcus epidermidis | SR1 | ssrA | S_epi-2 | TTG ATT ATA TTT CAT CTA AAC AGA CT | 60.0 | 3 |
| 10 | Staphylococcus epidermidis | SR1 | ssrA | S_epi-3 | CAG TTA TAT TTA ACC GAA ATG TGT | 61.2 | 3 |
| 11 | Klebsiella pneumoniae | MGH | ssrA | K_pneu-1 | ATT CCT ACA TCC TCG GCA | 60.1 | 4 |
| 12 | Klebsiella pneumoniae | MGH | ssrA | K_pneu-2 | GTC TTA AGA GCG GAA GCT AG | 59.0 | 4 |
| 13 | Klebsiella pneumoniae | MGH | ssrA | K_pneu-3 | AGC CTG ATT AGA TTT AAC GC | 59.3 | 4 |
| 14 | Enterococcus faecalis | 775 | ssrA | E_faeca-1 | CAT ATT GCC ACT TAA ATC TCT AC | 59.0 | 5 |
| 15 | Enterococcus faecalis | 775 | ssrA | E_faeca-2 | CTG TAT TGC TAG TCT GGT AAG CT | 60.9 | 5 |
| 16 | Enterococcus faecalis | 775 | ssrA | E_faeca-3 | ACA CTC ATT TAA AGG TTC GC | 59.5 | 5 |
| 17 | Pseudomonas aeruginosa | ATCC 25330 | ssrA | P_aeru-1 | GCT TAG CCA GCT CTA CTG AG | 59.4 | 6 |
| 18 | Pseudomonas aeruginosa | ATCC 25330 | ssrA | P_aeru-2 | TTA AGC AGC TAG AGC GTA GTT | 59.9 | 6 |
| 19 | Streptococcus pneumoniae | Type 4 | ssrA | S_pneu-2 | CTC AAG TCT AGA AAC TGC GAG | 59.4 | 8 |
| 20 | Streptococcus pneumoniae | Type 4 | ssrA | S_pneu-1 | TTA TTT TAA CAG CCC CTC G | 60.6 | 8 |
| 21 | Streptococcus mutans | UA159 | ssrA | S_mut-1 | TGT TTA TTT AAC ACC GTT ACA AT | 59.9 | 10 |

TABLE 1-continued

| SEQ ID NO: | Species | Reference Strain | Target Gene | Oligo Name | 5'-3' Sequence | Tm (° C.)* | Rank** |
|---|---|---|---|---|---|---|---|
| 22 | Streptococcus mutans | UA159 | ssrA | S_mut-2 | TCA AAC TCT AAC GAT GCG AG | 61.0 | 10 |
| 23 | Streptococcus gordonii | Not Known | ssrA | S_gord-1 | TGT TTT AAC TTG ATT TTG ACA CA | 60.7 | 10 |
| 24 | Streptococcus gordonii | Not Known | ssrA | S_gord-2 | CAA ATC AAG CGA GTC TAT CAA | 60.6 | 10 |
| 25 | Clostridium difficile | 630 | ssrA | C_diff-1 | CCA ACT TCA CTA ATA TCT CAC CT | 60.1 | 19 |
| 26 | Clostridium difficile | 630 | ssrA | C_diff-2 | GTC CAG TCT TAG TCG GCA G | 59.6 | 19 |
| 27 | Clostridium perfringens | (Shimizu) | ssrA | C_perf-1 | AGC AGA CCA GTA AGA CTT TCT AC | 59.7 | 19 |
| 28 | Clostridium perfringens | (Shimizu) | ssrA | C_perf-2 | AGA ACG TCC ACA GAC AAA CTT | 61.0 | 19 |
| 29 | Clostridium botulinum | Hall A | ssrA | C_bot-1 | AAC AGG CTC CTA GAT TCA GTA G | 60.1 | 19 |
| 30 | Clostridium botulinum | Hall A | ssrA | C_bot-2 | CCG AGT GCA GTT TAT CCT T | 59.7 | 19 |
| 31 | Haemophilus influenzae | Not Known | ssrA | H_infl-1 | GAC ACG CTA AAC TTA AGC TAG TT | 60.8 | 23 |
| 32 | Haemophilus influenzae | Not Known | ssrA | H_infl-2 | CCT CAA ACG GTG GCT TC | 60.7 | 23 |
| 33 | Enterococcus faecium | ATCC 35667 | ssrA | E_faeci-1 | GTC AAC TCA TTT AAG GAT TCA CT | 60.0 | 25 |
| 34 | Enterococcus faecium | ATCC 35667 | ssrA | E_faeci-2 | GAT GTT CTC TTT TTC AAC TTA CAG | 60.5 | 25 |
| 35 | Enterococcus durans | CNRZ129 | ssrA | E_dur-1 | TCA ACT CAT TTG AGG TTT CG | 60.5 | NR |
| 36 | Enterococcus durans | CNRZ129 | ssrA | E_dur-2 | TGA TGA TCT CTT TTA AAC TTT ACA G | 60.8 | NR |

TABLE 1-continued

| SEQ ID NO: | Species | Reference Strain | Target Gene | Oligo Name | 5'-3' Sequence | Tm (° C.)* | Rank** |
|---|---|---|---|---|---|---|---|
| 37 | Enterococcus durans | CNRZ129 | ssrA | E_dur-3 | AGG CAT TCT GTA TTG CTA GTC T | 60.6 | NR |
| 38 | Streptococcus pyogenes | M1 GAS SF370 | ssrA | S_pyo-1 | TTA TGT CTT CAT TTA ACA AAC TAA AG | 61.0 | NR |
| 39 | Streptococcus pyogenes | M1 GAS SF370 | ssrA | S_pyo-2 | TCA AGC CAT TAG TTT GCG | 59.8 | NR |
| 40 | Streptococcus pyogenes | M1 GAS SF370 | ssrA | S_pyo-3 | GAC AAT TTC GTA ACC GTA GC | 60.0 | NR |
| 41 | Streptococcus agalacticae | NCTC 8181 | ssrA | S_agal-1 | GTA TTG ATT TAA CTA GGT GAT GAC A | 60.8 | NR |
| 42 | Streptococcus agalacticae | NCTC 8181 | ssrA | S_agal-2 | TTA ACT AAC TAG ACA GTA GCC AAA C | 60.5 | NR |
| 43 | Escherichia coli | O157:H7 EDL933 | ssrA | Eco_ssrA_DP50 | TCA GTC TTT ACA TTC GCT TGC CAG CTG CGG ACG GAC ACG CCA CTA ACA AA | 75.0 | 2 |
| 44 | Staphylococcus aureus | NCTC 8325 | ssrA | Sau_ssrA_DP50 | CTT CAA ACG GCA GTG TTT AGC ATA TCC TAT TAA GGT TGA ATC GCG TTA AC | 70.0 | 1 |
| 45 | Staphylococcus epidermidis | SR1 | ssrA | Sep_ssrA_DP50 | CCA ACA TGA TAC TAG CTT GAT TAT ATT TCA TCT AAA CAG ACT TCA AGC GG | 69.0 | 3 |
| 46 | Escherichia coli | O157:H7 | rnp | EcoCP4 | GCA CTG GTC GTG GGT TTC | 63.2 | 2 |
| 47 | Staphylococcus aureus | WCUH29 | rnp | SauCP5 | TTA CTC TAT CCA TAT CGA AAG ACT | 59.9 | 1 |
| 48 | Staphylococcus epidermidis | SR1 | rnp | SepCP6 | CTA TTC TAA CCA TAT CCA ATG ACT | 60.0 | 3 |

TABLE 1-continued

| SEQ ID NO: | Species | Reference Strain | Target Gene | Oligo Name | 5'-3' Sequence | Tm (° C.)* | Rank** |
|---|---|---|---|---|---|---|---|
| 49 | Escherichia coli | O157:H7 | rnp | Eco_rnp_DP50 | CCC CCC AGG CGT TAC CTG GCA CCC TGC CCT ATG GAG CCC GGA CTT TCC TC | 77.0 | 2 |
| 50 | Staphylococcus aureus | WCUH29 | rnp | Sau_rnp_DP50 | TAG GAT ATT TCA TTG CCG TCA AAT TAA TGC CTT GAT TTA TTG TTT CAT CA | 67.0 | 1 |
| 51 | Staphylococcus epidermidis | SR1 | rnp | Sep_rnp_DP50 | TAG GTT ATT TCA TTG CCG TCA AAT TAA TGC CTT GAT TTA TTG TTT CAT CA | 67.0 | 3 |
| 52 | Escherichia coli | K12 | 16S rRNA | EcoCP7 | AGT GTG GCT GGT CAT CCT | 59.0 | 2 |
| 53 | Escherichia coli | RREC I | 16S rRNA | Eco_16_DP50 | CTC AGA CCA GCT AGG GAT CGT CGC CTT GGT GAG CCG TTA CCC CAC CAA CA | 75.0 | 2 |

*Nearest neighbor analysis
**Ranking of species in top 25 (US) blood pathogens; NR = not ranked within top 25 US blood pathogens For the purposes of present invention, a capture probe captures (by binding to) an oligonucleotide from a sample by hybridizing with it at a sequence (e.g., a capture sequence) that is at least partially complementary to a sequence (e.g., a target sequence) of the oligonucleotide being captured. Likewise, a detector probe detects (by binding to) an oligonucleotide from a sample by hybridizing with it at a sequence (e.g., a capture sequence) that is at least partially complementary to a sequence of the oligonucleotide being captured (e.g., a target sequence). As used herein, the phrase "partially complementary" means less than 100% complementary, but at least about 85% complementary. Accordingly, the phrase "at least partially complementary" indicates that the capture sequence of a capture and/or detector probe may between about 85% complementary to about 100% complementary to a target sequence to be useful according to the present invention. A capture sequence and a target sequence of an oligonucleotide to be captured may be, as non-limiting examples, at least about 85%, at least about 90%, at least about 95%, at least about 96%, at least about 97%, at least about 98%, at least about 99%, or about 100% complementary to one another. For example, if a capture sequence is 100 bases long, and the target sequence is 95% complementary to the capture sequence, the base pairs of the capture sequence and the target sequence will match in 95 of 100 bases of the capture sequence.

As a practical matter, whether any particular nucleic acid molecule is at least 85%, at least 90%, at least 95%, at least 96%, at least 97%, at least 98%, at least 99%, or 100% complementary to a target nucleic acid can be determined conventionally using known computer programs such as, for example, the Bestfit program (Wisconsin Sequence Analysis Package, Version 8 for Unix, Genetics Computer Group, Wisconsin, USA). Bestfit uses the local homology algorithm of Smith and Waterman, *Advances in Applied Mathematics* 2:482-489 (1981), to find the best segment of homology between two sequences. When using Bestfit or any other sequence alignment program to determine whether a particular sequence is, for example, 95% complementary to a reference sequence according to the present invention, the parameters are set such that the percentage of identity is calculated over the full length of the reference nucleotide sequence, whether that be the capture probe or the target nucleic acid, and that gaps in similarity of up to 5% of the total number of nucleotides in the reference sequence are allowed.

Whether the capture sequence of a capture probe and/or detector probe will hybridize to the target sequence of a target oligonucleotide depends on the degree of complementarity between the target sequence and the capture sequence, as well as both the hybridization conditions and the stringency of the wash after hybridization. As used herein, the phrase "conditions that permit hybridization" refers to hybridization parameters, as well as wash parameters, that permit hybridization between two oligonucleotides, as are understood in the art. For example, conditions that permit hybridization include, but are not limited to, more stringent hybridization and wash conditions, such as incubation at 42° C. in a solution comprising 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing with 0.1×SSC at about 65° C., 68° C. or 70° C. Of course, hybridization and wash conditions can be set to a lower stringency. Lower stringency hybridization and wash conditions include, but are not limited to, incubation at 42° C. in a solution comprising 30% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in a solution of 2×SSC or 1×SSC or 0.5×SSC at about 55° C. or 60° C. or 65° C. As is within the capacity of one of ordinary skill in the art, the conditions to permit hybridization can be easily and routinely optimized to require a lower or higher degree of complementarity between a capture probe and/or detector probe and a target nucleic acid before hybridization will occur. For example, anionic detergents such as sodium dodecyl sulfate (SDS) may be used to enhance the stringency of hybridization or washing, and exclusion molecules such as PEG may be used to increase the effective concentration of reaction components.

A capture probe or detector probe may be an oligonucleotide or a polynucleotide, as these terms are understood in the art. A capture probe or detector probe may be, for example, at least 10, 15, 20, 25, 30, 35, 40, 45, 50, 75, 100, 150, 200, 300, 400, 500 or 750 nucleotides in length. For convenience, the term "oligonucleotide" as used herein encompasses all of these lengths. In some embodiments, capture probes and/or detector probes may be up to and including about 2000 nucleotides in length. In some embodiments, capture probes and/or detector probes are about 15 to about 60 nucleotides in length.

The length of the capture probe and/or detector probe and the capture sequence(s) thereof and the conditions of hybridization may be tailored to form a specific complex with the nucleic acid of the intended target. The stability of a hybrid complex, commonly measured by its melting temperature, is related to the concentration of the probe, the hybridization conditions, the length of the hybrid complex and the degree of sequence identity between the capture sequence and the target sequence. The stability of a hybrid complex is decreased by mismatches and is increased by the number of base pairs in the hybrid complex. Such relationships are detailed, for example, in Sambrook et al., MOLECULAR CLONING: A LABORATORY MANUAL, 3$^{rd}$ ed., Cold Spring Harbor Laboratory Press, New York (2001), which is herein incorporated by reference. A probe can be used to distinguish between closely related sequences that differ in the hybrid complex by as little as a single base. That is, a probe may be perfectly matched with a target nucleic acid from one species of microorganism but may differ in sequence by one base with the nucleic acid target of a second species, for example. Under the appropriate conditions, the presence of the mismatch causes the probe to form a hybrid complex with one target but not with the other. Because the relative difference in melting temperature between the matched and mismatched complexes decreases with increasing size of the probe, the probe preferably should be 25 bases in length or less to detect a single mismatch. See Sambrook et al. While longer probes can be used to discriminate between closely related targets, the targets preferably should diverge to a progressively greater extent as the size of the probe increases.

After a hybrid complex is formed, the methods of the present invention then detect the hybrid complex. If a hybrid complex is detected, the presence of the hybrid complex indicates that the target sequence was released from a microorganism in the sample tested. Accordingly, the presence of a hybrid complex indicates the presence in the sample of the microorganism and/or epidemiological marker containing the target sequence. In contrast, when a hybrid complex is not detected, the absence of the hybrid complex indicates that the target sequence was not released from a microorganism in the sample tested. Accordingly, the absence of a hybrid complex indicates that the sample most likely does not contain the microorganism and/or epidemiological marker containing the target sequence.

Any method of detecting the hybrid complex can be used in the present invention, provided that one of skill in the art can rely on the detection methods to identify the presence of a hybrid complex. In some embodiments, at least one detector probe, in addition to the capture probe, is used to detect the hybrid complex. The detector probe hybridizes to a single-stranded portion (or "target sequence") of the target nucleic acids that are captured.

A detector probe may comprise a reporter group to facilitate detection. As used herein, a "reporter group" means an entity that can generate a detectable signal. A reporter group may be incorporated into a detector probe, a reporter group may be directly linked or bound to a detector probe, or a reporter group may be indirectly linked or bound to a detector probe. As explained in more detail hereinabove, as an example of an indirect attachment using a linker molecule, a detector probe may comprise a reporter adapter sequence linker, which is capable of binding via hybridization to a reporter probe, which is bound to a reporter group. Detector probes that "comprise" reporter groups include detector probes that have a reporter group, reporter adapter sequence linkers, and the like incorporated therein, as well as detector probes that are directly or indirectly linked or bound to reporter groups, reporter adapter sequence linkers, and the like.

Many different reporter groups are known in the art. For example, radioactive isotopes may be used as reporter groups. Radioactive isotopes may be, for example, incorporated into or attached to a detector probe, thereby generating a radioactive probe. Examples of a radioactive isotopes that can be used as reporter groups include, but are not limited to $^{32}$P, $^{33}$P $^{131}$I, $^{90}$Y, $^{188}$Re, $^{186}$Re, $^{67}$Cu, $^{198}$Au, $^{103}$Pd and $^{212}$Pb/$^{212}$Bi.

Enzymes and/or enzyme systems that can be used to generate a detectable signal may also be used as reporter groups. Enzymes and/or other components of enzyme systems can be attached directly to a detector probe or can attach indirectly to a detector probe. For example, a detector probe may be biotinylated. As a specific, non-limiting example, a detector probe may be bound to BioTEG, which is biotin with a 15 atom tetra-ethyleneglycol spacer. Biotin possesses the ability to bind to avidin or streptavidin. Continuing the example, an enzyme such as horseradish peroxidase would be conjugated to avidin or streptavidin, thereby allowing the horseradish peroxidase to localize to the hybrid complex via binding of the biotin of the biotinylated detector probe and the avidin of the avidin-enzyme conjugate. Upon addition of a substrate, horseradish peroxidase would then generate a detectable colorimetric signal as is readily understood in the art. Additional examples of enzymes that may be used as reporter groups include, but are not limited to alkaline phosphatase, glucose oxidase, β-galactosidase, soybean peroxidase and luciferase.

Fluorescent or other detectable molecules may also be used as reporter groups and may be attached directly or indirectly to the detector probe. Non-limiting examples of detectable molecules that may be used as reporter groups include, but are not limited to, fluorescein, fluorescein isothiocyanate (FITC), rhodamine red, ROX™ (Invitrogen, California, USA), Cy™ dyes (Amersham, New Jersey, USA), Bodipy™ dyes (Molecular Probes, Oregon, USA), TAMRA™ dyes (Molecular Probes, Oregon, USA), TET™ (Molecular Probes, Oregon, USA), Texas Red® (Molecular Probes, Oregon, USA), europium dyes, chromogenic moieties and green fluorescent protein (GFP).

Reporter groups may also comprise an "amplification sequence," i.e., a nucleotide sequence that can initiate nucleic acid amplification. For example, an amplification sequence may be appended to a detector probe, or an amplification sequence may be an integral part of a detector probe. An amplification sequence can initiate nucleic acid replication, or amplification, using any form of amplification including, but not limited to, strand displacement amplification (SDA), polymerase chain reaction (PCR), reverse transcriptase-strand displacement amplification (RT-SDA), reverse transcriptase-polymerase chain reaction (RT-PCR), nucleic acid sequence based amplification (NASBA), MessageAmp™ amplification (Ambion, Inc., Texas, USA), transcription-mediated amplification (TMA), rolling circle amplification, and Qβ replicase amplification. The nucleic acids may be amplified prior to contacting them with a capture probe or after they are contacted with the capture probe.

Instead of or in addition to the use of a detector probe, a hybrid complex may also be detected using such standard methods as non-specifically labeling the hybrid complex. For example, intercalating dyes, such as ethidium bromide, may be used to label the hybrid complex for detection. Other examples of non-specific labeling of the hybrid complex include, but are not limited to, acridine orange, SYBR™ Green I/II (Molecular Probes, Oregon, USA), SYBR Gold, propidium iodide and cyanine monomers or dimers.

In some embodiments, the methods and/or probes of the present invention are used to monitor the efficacy of antimicrobial patient therapy by sequential sampling of specimens over time. The detection of mRNA has been correlated with microbial viability. Hellyer et al., *J. Clin. Microbiol.* 37: 290-295 (1999). Accordingly, the detection of RNA in a first sample, followed by administration of antimicrobial therapy and subsequent failure to detect RNA in a second sample, most likely indicates a successful response to therapy. In contrast, detection of RNA in the second sample would most likely indicate the continued presence of viable organisms in the specimen, and the need for continued therapy or a change in therapeutic regimen.

In some other embodiments, the methods and/or probes of the present invention are used to quantify the number of organisms in a sample through the use of an internal standard and by comparison of signal intensities with controls. The internal standard may be RNA or DNA that is free in solution or encapsulated, such as in an Armored RNA™ (Ambion Diagnostics, Texas, USA) particle or recombinant bacterium, to protect against degradation. The internal standard may be seeded into the sample at any point prior to detection. In some embodiments, the internal standard is seeded in the sample prior to concentration and lysis of the microorganism(s). The internal standard is detected using specific capture probes that permit distinction of the standard from target nucleic acid and from other nucleic acids that may be present. The signal generated by the internal standard in the test sample is compared to that from controls that comprise different levels of the standard nucleic acid conjugated directly to the solid phase. By plotting a curve of signal intensities for the controls, the proportion of the internal standard recovered from the specimen may be calculated. In similar fashion, controls comprising different levels of the target sequence conjugated directly to the solid phase may be used to quantify the amount of target present in the processed sample. By correcting for recovery of nucleic acid using the internal standard, the quantity of target nucleic acid in the original sample may then be calculated.

It is important to note that the methods of the present invention also have application outside the fields of human and animal infectious disease and are particularly suited to applications requiring rapid, sensitive and specific detection and/or identification of multiple analytes. Accordingly, the methods of the present invention can be used to detect microorganisms in samples in many fields including, as non-limiting examples, therapeutic monitoring, food and environmental testing and monitoring deployment of weapons of bioterrorism.

The present invention also relates to kits for detecting the presence or absence of at least one microorganism in a sample. The kits comprise a solid support, as defined hereinabove, comprising at least one capture probe, also defined hereinabove. The at least one capture probe may be a microorganism-specific probe, a probe that is for an epidemiological marker, and/or a probe that is for a drug resistance marker. The kits of the present invention also comprise at least one reporter group, as previously described hereinabove. The kits may also comprise a vessel. The vessel can be used to collect or concentrate the sample and/or to isolate the nucleic acids released from the microorganisms. The vessels may also be used when amplifying the nucleic acids released from the microorganism, if desired or necessary. Examples of vessels include, but are not limited to, evacuated blood collection tubes, eppendorf tubes, test tubes, etc. The kits may further comprise enzymes or other chemicals, such as media, detergents, buffers, acids, bases, and chaotropes used to lyse the microorganisms present in the sample. The reporter group(s) of the kits further comprises at least one detector probe. In such embodiments, the reporter group may be incorporated into or onto the detector probe, as previously described herein. As with the capture probe, the detector probe may be a universal probe or a species-specific probe. Kits of the present invention may also comprise positive, negative, and/or internal controls. In certain embodiments, kits of the present invention may comprise a sufficient number of probes and/or amounts of other components to permit the performance of only a single assay or group of related assays using probes according to the present invention. In other embodiments, kits of the present invention may comprise a sufficient number of probes and/or amounts of other components to permit the performance of multiple assays using probes according to the present invention.

The Figures provide non-limiting exemplary illustrations of embodiments of the present invention and devices and non-limiting exemplary sequences useful in practicing the present invention. One exemplary embodiment of the probes and methods of the present invention is illustrated in FIG. 1. In FIG. 1, bacteria in blood are concentrated into a volume of 300 μL using a Wampole isolator tube. Next, the bacteria are lysed to release RNA or DNA, and this RNA- and/or DNA-containing solution in either a crude or purified form is applied to a microarray solid support that has capture probes immobilized thereto. The capture probes may be, for example, microorganism-specific probes, probes that are for epidemiological markers, and/or probes that are for drug resistance markers. In this particular embodiment, after the microbial RNA and/or DNA is allowed to hybridize with the capture probes to form hybrid complexes, the complexes are detected using a detector probe that bears a reporter group.

Two exemplary embodiments of the use of the probes and methods of the present invention are illustrated in FIGS. 2A and 2B. The two embodiments of FIG. 2 differ in the manner in which capture probes are immobilized on a solid support. The capture probes of the embodiment illustrated in FIG. 2A are immobilized directly on the solid support. The capture probes are species-specific, and species A-specific capture probes are immobilized to one spot (A), while species B-specific capture probes are immobilized to a different spot (B). In a further embodiment, two or more capture probes may be immobilized on a single spot to permit the capture and detection of two or more target sequences derived from different organisms in a single location.

In contrast, the capture probes of the embodiment illustrated in FIG. 2B are immobilized indirectly on the solid support through the use of immobilization probes. Each species-specific capture probe comprises an immobilization sequence that is hybridized to an immobilization probe. The immobilization probe is immobilized to a spot on the solid support. Each of the immobilization probes of the embodiment illustrated in FIG. 2B is specific for a specific type of capture probe. Immobilization probes A hybridize specifically to capture probes A (which are specific for species A), and immobilization probes B hybridize specifically to capture probes B (which are not shown, but which are specific for species B). Capture probe A-specific immobilization probes are immobilized to one spot (A), while capture probe B-specific immobilization probes are immobilized to a different spot (B). In a further embodiment, two or more immobilization probes may be immobilized on a single spot to permit the capture and detection of two or more target sequences derived from different organisms in a single location.

In each of the embodiment of FIG. 2A and the embodiment of FIG. 2B, a first target sequence of a target oligonucleotide released from microorganism species A hybridizes to a species A-specific capture sequence on a species A-capture probe, forming a hybrid complex. The hybrid complex is detected by allowing a second target sequence on the target oligonucleotide to hybridize to a species A-specific capture sequence on a species A-specific detector probe. A reporter adapter sequence on the detector probe is allowed to hybridize with a universal reporter probe having a reporter group attached thereto.

Immobilization probe-capture probe combinations may be varied and customized, however. As just one non-limiting example, using FIG. 2B for illustrative purposes, the immobilization probes specific for species A-specific capture probes could also bind to capture probes specific for a second species ("species C"). Species C could be, for example, of the same genus as species A. In such a case, species A-specific capture probes and species C-specific capture probes would comprise the same immobilization sequences, while having capture sequences specific for species A or C, respectively.

FIG. 3 depicts an exemplary solid support that may be used to immobilize probes of the present invention and may be used in the methods and kits of the present invention. The solid support illustrated in FIG. 3 is a flow-through microarray chip, which has the advantage of increasing the rate of hybridization between the capture probe and the RNA and/or DNA of the microorganism. The flow-through chip illustrated in FIG. 3 was produced by MetriGenix, Inc. (Maryland, USA).

FIG. 4 depicts a vessel capable of concentrating the microorganisms in a sample, such as blood, that can be used in the methods and kits of the present invention.

FIGS. 5A-C illustrate embodiments of the invention in which immobilization probes comprising sequences from the human genes K-alpha (tubulin alpha-1), PPIA (peptidylprolyl isomerase A), and UBC (ubiquitin-conjugating enzyme E2A) are immobilized onto different regions (or "spots") of a solid support. Each of the immobilization probes is hybridized to an oligonucleotide capture probe comprising (1) an immobilization sequence complementary to the immobilization probe and (2) and an organism-specific capture sequence. The capture sequences of the capture probes are designed to hybridize to sequences that are specific for E. coli, S. aureus or S. epidermidis. An E. coli, S. aureus or S. epidermidis target oligonucleotide is bound to each capture probe via hybridization between a capture sequence of the capture probe and a first target sequence of the target oligonucleotide.

A biotinylated detector probe is bound to each target oligonucleotide via hybridization between a capture sequence of the detector probe and a second target sequence of the target oligonucleotide. Streptavidin conjugated to horseradish peroxidase enzyme is bound to the biotin molecules of the biotinylated detector probes. A horseradish peroxidase enzyme substrate is added, and a detectable signal is generated.

FIG. 6 depicts synthetic target oligonucleotides derived from discontiguous regions within the ssrA genes (small stable RNA A) of E. coli, S. aureus, and S. epidermidis. Target sequences in the target oligonucleotides are underlined or boxed. Capture probes and detector probes that may be used to capture and detect these sequences are also shown, and their capture sequences are underlined or boxed. Specifically, regions of complementarity between capture probes and target nucleic acids are underlined, and regions of complementarity between detector probes and target nucleic acids are boxed. The capture probes also comprise immobilization sequences from the human genes K-alpha (tubulin alpha-1), PPIA (peptidylprolyl isomerase A), and UBC (ubiquitin-conjugating enzyme E2A). These human gene sequences (SEQ ID NOs:59, 65, and 71) are italicized in FIG. 6 and set forth in Table 4a, hereinbelow. FIG. 6 is described in more detail in the examples hereinbelow.

FIG. 7F depicts the arrangement of immobilization probes and controls on chips according to the invention. FIGS. 7A-E depict results from exemplary assays using probes and methods according to the invention. FIGS. 7A-F are described in more detail in the examples hereinbelow.

Figure 8C:
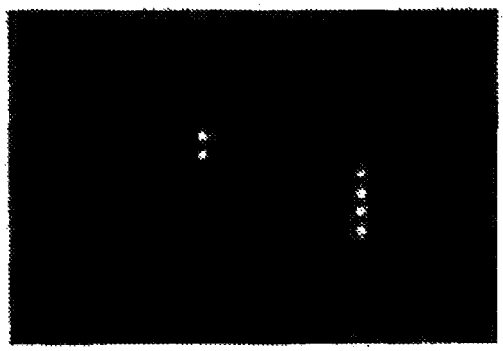

FIG. 8A depicts the arrangement of capture probes and controls on chips according to the invention. FIGS. 8B-E depict results from exemplary assays using probes and methods according to the invention. FIGS. 8A-E are described in more detail in the examples hereinbelow.

The following experimental examples are provided to illustrate certain embodiments of the invention, but are not intended to limit the invention. The examples and embodiments described herein are illustrative, but not limiting, of the probes, methods and kits of the present invention. Other suitable modifications and adaptations of the variety of conditions and parameters normally encountered in typical laboratory and which are obvious to those skilled in the art are within the spirit and scope of the invention described herein.

Example 1

Determination of the Specific Gravities of *E. Coli, S. Aureus* and *C. Albicans* in Comparison to Whole Human Blood To prepare a density gradient, 60% iodixanol (1.32 g/ml) was diluted with Dulbecco's phosphate buffered saline to densities of 1.080, 1.101, 1.121 and 1.143 g/ml. A 2-ml volume of each of the density solutions was sequentially added to a conical centrifuge tube in order of density, starting with the highest.

A 1.25-ml volume of anticoagulated whole human blood was diluted 4-fold with Dulbecco's phosphate-buffered saline. The diluted blood was inoculated with *E. coli, S. aureus* or *C. albicans* at a final concentration of 2500 organisms/ml. The organism-spiked blood was overlayered on the density gradient. The gradient was centrifuged at 3000×g for 20 minutes at ambient temperature. Following centrifugation, 2 ml fractions were removed from the density gradient. A 0.1-ml volume of each fraction was pipetted onto a blood agar plate and streaked for organism isolation. Each plate was incubated for approximately 18 hours at 35° C. under ambient air.

*E. coli* and *S. aureus* were isolated from the fractions with densities of between 1.101 and 1.121 and 1.121 and 1.143 g/m, respectively. *C. albicans* was isolated from the fraction with a density of 1.143 g/ml. Blood cells were observed in the fraction with a density between 1.080 and 1.101 g/ml. The latter data are consistent with reports in the literature, in which the density of blood is estimated to be 1.090-1.101 g/ml. These data demonstrate that organisms can be differentially separated from blood in a density solution provided that their specific gravity is higher than that of blood.

Example 2

Differential Separation of *S. Aureus* and *C. Albicans* from Blood in a Density Solution A 5-ml volume of anticoagulated whole human blood was inoculated with *S. aureus* or *C. albicans* at a final concentration of 2500 organisms/ml. After inoculation, a 2-ml volume was overlayered on a 3-ml volume of density solution at 1.090 g/ml, prepared by dilution of 60% (1.32 g/ml) iodixanol with Dulbecco's phosphate-buffered saline. The density solution was centrifuged at 5445×g for 40 minutes at ambient temperature. After centrifugation, 1-ml fractions were collected from the density solution. The organisms were isolated from the density fractions as described in Example 1. In contrast, the blood cells were observed to remain at the top of the density solution.

These data demonstrate that both *S. aureus* and *C. albicans* can be separated from whole blood by centrifugation through a density matrix. These organisms can be further processed to purify protein, DNA or RNA and be used in downstream molecular or microbiological applications.

Example 3

Differential Separation of *E. Coli, S. Aureus* and *C. Albicans* from Lysed Human Blood A 5-ml volume of whole human blood was lysed with Triton X-100 at a final concentration of 1%. The detergent-treated blood was inoculated with *E. coli, S. aureus* or *C. albicans* at a final concentration 2500 organisms/ml. Sixty percent iodixanol (1.32 g/ml) was diluted to 1.090 g/ml with Dulbecco's phosphate-buffered saline. A 3-ml volume of density solution at 1.090 g/ml was overlayered with a 2-ml volume of lysed blood containing the three organisms. The density solution was centrifuged and fractions were collected as described in Examples 1 and 2. The organisms were isolated from the fractions as described in Example 1. All three organisms were recovered from the bottom of the density solution. Meanwhile, the debris from the lysed blood cells was observed at the top of the density solution.

These data show that *E. coli, S. aureus* and *C. albicans* can be separated efficiently from blood that has been lysed in Triton X-100. As described in Example 2, recovered organisms can be used in subsequent downstream molecular or microbiological applications.

Example 4

Detection of *E. Coli*-, *S. Aureus*-, and *S. Epidermidis*-Specific Oligonucleotides Using MGX® Universal Chips The following example demonstrates the detection of *E. coli*-, *S. aureus*- and *S. epidermidis*-specific synthetic oligonucleotides using the MetriGenix® 4D™ DNA chip.

MetriGenix® chips (MetriGenix, Inc., Maryland, USA) were spotted with immobilization probes of approximately 60 nucleotides in length comprising sequences from the human genes K-alpha (tubulin alpha-1) (SEQ ID NO:84), PPIA (peptidylprolyl isomerase A) (SEQ ID NO:85), and UBC (ubiquitin-conjugating enzyme E2A) (SEQ ID NO:86). The sequences of the immobilization probes (SEQ ID NOs: 84-86) are set forth in Table 4b. The locations of the immobilization probes immobilized on the chips are shown in FIG. 7F. Also included on each chip were negative ("buffer") and positive ("staining") control spots that were prepared by spotting of buffer or immobilization of a biotinylated beta-actin-derived oligonucleotide, respectively. The "buffer" spots served as negative controls for non-specific hybridization. The "staining" spots served as positive staining controls for the chemiluminescent detection reaction. The sequence of the positive staining control biotinylated beta-actin-derived oligonucleotide (SEQ ID NO:83) was as follows: 5'-CCC AGG GAG ACC AAA AGC-Biotin. Each of the chips used in this example (Chips A-E) bore the indicated capture probes in the arrangement indicated in FIG. 7F.

Each of the immobilization probes was hybridized to an oligonucleotide capture probe comprising (1) an immobilization sequence of approximately 30 bases complementary to the immobilization probe and (2) and an organism-specific ssrA gene capture sequence of about 20-nucleotides. The sequences of the capture probes (SEQ ID NOs:55, 61, 67) are set forth in Table 2 and in FIG. 6.

The capture sequences of the capture probes were designed to hybridize to sequences that are specific for *E. coli, S. aureus*, or *S. epidermidis*. The capture sequences (SEQ ID NOs:1, 6, 10) of the capture probes are underlined in FIG. 6 and set forth in Table 3. The capture probe specific for *E. coli* also comprises an immobilization sequence (SEQ ID NO:59; italicized in FIG. 6 and set forth in Table 4a) complementary to the K-alpha immobilization probe. The capture probe specific for *S. aureus* also comprises an immobilization sequence (SEQ ID NO:65; italicized in FIG. 6 and set forth in Table 4a) complementary to the PPIA immobilization probe. The capture probe specific for *S. epidermidis* also comprises an immobilization sequence (SEQ ID NO:71; italicized in FIG. 6 and set forth in Table 4a) complementary to the UBC immobilization probe. (See FIGS. 5A-C for a schematic illustration.)

TABLE 2

Sequences of Capture Probes Used in Example 4

| Target Organism | Target Gene | 5'-3' Probe Sequence | SEQ ID NO: |
|---|---|---|---|
| *E. coli* | ssrA | TCC TCG GTA CTA CAT GCT TAG TAC ATT CAA CAG AAT CCA CAC CAA CCT CCT CAT A | 55 |
| *S. aureus* | ssrA | TTG ATT AAG TTT CTT CTA AAC AGA TAC ATC ATA ATC ATA AAC TTA ACT CTG CAA TCC A | 61 |
| *S. epidermidis* | ssrA | CAG TTA TAT TTA ACC GAA ATG TGT ACA GAA AGT GCA ATG AAA TTT GTT GAA ACC TTA | 67 |

TABLE 3

Capture Sequences of Capture Probes Used in Example 4

| Target Organism | Target Gene | 5'-3' Probe Sequence | SEQ ID NO: |
|---|---|---|---|
| *E. coli* | ssrA | TCC TCG GTA CTA CAT GCT TAG | 6 |
| *S. aureus* | ssrA | TTG ATT AAG TTT CTT CTA AAC AGA | 1 |
| *S. epidermidis* | ssrA | CAG TTA TAT TTA ACC GAA ATG TGT | 10 |

TABLE 4a

Immobilization Sequences of Capture Probes Used in Example 4

| Capture Probes' Target Organism and Gene | Immobilization Sequence Corresponds to Portion of Human Gene Sequence | 5'-3' Probe Sequence | SEQ ID NO: |
|---|---|---|---|
| *E. coli* ssrA | K-alpha | TTC AAC AGA ATC CAC ACC AAC CTC CTC ATA | 59 |
| *S. aureus* ssrA | PPIA | TCA TAA TCA TAA ACT TAA CTC TGC AAT CCA | 65 |
| *S. epidermidis* ssrA | UBC | GAA AGT GCA ATG AAA TTT GTT GAA ACC TTA | 71 |

TABLE 4b

Immobilization Probes Used in Example 4

| Used to Immobilize Capture Probe Specific for Target Organism and Gene | Immobilization Probe Corresponds to Portion of Human Gene Sequence | 5'-3' Probe Sequence | SEQ ID NO: |
|---|---|---|---|
| *E. coli* ssrA | K-alpha | CGT GAA GAT ATG GCT GCC CTT GAG AAG GAT TAT GAG GAG GTT GGT GTG GAT TCT GTT GAA | 84 |
| *S. aureus* ssrA | PPIA | ATG TTT TCC TTG TTC CCT CCC ATG CCT AGC TGG ATT GCA GAG TTA AGT TTA TGA TTA TGA | 85 |
| *S. epidermidis* ssrA | UBC | TGG TCC TGC GCT TGA GGG GGG GTG TCT AAG TTT CCC CTT TTA AGG TTT CAA CAA ATT TCA TTG CAC TTT C | 86 |

To mimic the presence of microorganism-derived target oligonucleotides in a sample, synthetic target oligonucleotides comprising first target sequences complementary to the capture sequences of the capture probes specific for each organism were used to flood the MetriGenix® chip. The sequences of the synthetic target oligonucleotides (SEQ ID NOs:54, 60, 66) are set forth in Table 5 and in FIG. 6. The synthetic target oligonucleotides were bound to (or "captured by") the organism-specific immobilization probes via hybridization between the capture sequence of the capture probe and the first target sequence of the synthetic target oligonucleotide. (See FIGS. 5A-C for a schematic illustration.) The sequences of the first target sequences (SEQ ID NOs:57, 63, 69) of the synthetic target oligonucleotides are underlined in FIG. 6 and set forth in Table 6.

biotin labels attached to the detector probes are also shown in Table 8 and in FIG. 6. Detection of a captured synthetic target oligonucleotide occurred through hybridization between the second target sequence of the synthetic target oligonucleotide (SEQ ID NOs:58, 64 or 70) and the capture sequence of the detector probe specific for that target oligonucleotide (SEQ ID NOs:1, 6 or 10). Therefore detector probes specific for captured target oligonucleotides were immobilized. Unbound detector probes were removed by washing. Streptavidin—linked horseradish peroxidase and an appropriate chemiluminescent substrate (Luminol) were then added. The streptavidin—linked horseradish peroxidase was bound to immobilized biotin-bearing detector probes via bonding between streptavidin and biotin. In the presence of hydrogen

TABLE 5

Sequences of Synthetic Target Oligonucleotides Used in Example 4

| Organism | Gene | 5'-3' Target Oligonucleotide Sequence | SEQ ID NO: |
|---|---|---|---|
| E. coli | ssrA | TCC CTA GCC TCC GCT CTT AGG ATA AAG ACT GAC TAA GCA TGT AGT ACC GAG GAT | 54 |
| S. aureus | ssrA | AAG TCT GTT TAG AAG AAA CTT AAT CAA ACT AGC ATC ATG TTG GTT GTT TAT CAC TTT TCA TGA TGC | 60 |
| S. epidermidis | ssrA | AAC ACA TTT CGG TTA AAT ATA ACT GAC AGT ATC ATG TTG GTT GTT TAT TGC TTA GCA TGA TGC GA | 66 |

TABLE 6

First Target Sequences of Synthetic Target Oligonucleotides Used in Example 4

| Organism | Gene | 5'-3' Target Oligonucleotide Sequence | SEQ ID NO: |
|---|---|---|---|
| E. coli | ssrA | CTA AGC ATG TAG TAC CGA GGA | 57 |
| S. aureus | ssrA | TCT GTT TAG AAG AAA CTT AAT CAA | 63 |
| S. epidermidis | ssrA | ACA CAT TTC GGT TAA ATA TAA CTG | 69 |

The synthetic target oligonucleotides also comprised second target sequences (SEQ ID NOs:58, 64, 70; boxed in FIG. 6 and set forth in Table 7) that were complementary to the organism-specific capture sequences of 5'-biotinylated detector probes. The sequences of the detector probes (SEQ ID NOs:56, 62, 68) are set forth in Table 8 and in FIG. 6. The 5' peroxide, horseradish peroxidase catalyzes the oxidation of the substrate Luminol, resulting in the emission of light that is captured by a Charge-Coupled Device (CCD) camera. (See FIGS. 5A-C for a schematic illustration.) The capture sequences (SEQ ID NOs:2, 7, 8) of the detector probes are boxed in FIG. 6 and set forth in Table 9.

TABLE 7

Second Target Sequences of Synthetic Target Oligonucleotides Used in Example 4

| Organism | Gene | 5'-3' Target Oligonucleotide Sequence | SEQ ID NO: |
|---|---|---|---|
| E. coli | ssrA | TAG CCT CCG CTC TTA GGA | 58 |
| S. aureus | ssrA | GGT TGT TTA TCA CTT TTC ATG A | 64 |
| S. epidermidis | ssrA | TTG TTT ATT GCT TAG CAT GAT GC | 70 |

TABLE 8

Sequences of Detector Probes Used in Example 4

| Target Organism | Target Gene | 5'-3' Probe Sequence | SEQ ID NO: labeled with biotin |
|---|---|---|---|
| E. coli | ssrA | Biotin-CAC TAC GAC TCT CGG TCT GAT TCT ATT TGC TCC TAA GAG CGG AGG CTA | 56 |
| S. aureus | ssrA | Biotin-CAC TAC GAC TCT CGG TCT GAT TCT ATT TGC TCA TGA AAA GTG ATA AAC AAC C | 62 |
| S. epidermidis | ssrA | Biotin-CAC TAC GAC TCT CGG TCT GAT TCT ATT TGC CAT CAT GCT AAG CAA TAA ACA A | 68 |

TABLE 9

Capture Sequences of Detector Probes Used in Example 4

| Target Organism | Target Gene | 5'-3' Probe Sequence | SEQ ID NO: |
|---|---|---|---|
| E. coli | ssrA | TCC TAA GAG CGG AGG CTA | 7 |
| S. aureus | ssrA | TCA TGA AAA GTG ATA AAC AAC C | 2 |
| S. epidermidis | ssrA | CAT CAT GCT AAG CAA TAA ACA A | 8 |

The sample mix loaded onto to each of the chips used in this example (Chips A-E) contained 10 nM organism-specific capture probe, 100 nM biotinylated organism-specific detector probe, and 50 nM target oligonucleotide. The sample mix containing the target oligonucleotides and probes was heated on a 95° C. heat block for five minutes and immediately cooled on ice for two minutes. Reagents were flowed sequentially through MetriGenix® chips as follows using an MGX® 2000 hybridization station (MetriGenix, Inc., Maryland, USA):

a. 2500 μL Buffer 1 (saline sodium phosphate-EDTA (SSPE) containing Triton X-100) at a flow rate of 500 μL/min;
b. Blocking Reagent (buffered goat serum); 6 min at a flow rate of 10 μL/min;
c. 1250 μL Buffer 2 (morpholinoethane sulfonic acid buffer (MES) containing formamide, EDTA, sarcosine and NaCl) at a flow rate of 500 μL/min;
d. Hybridization Mixture (Buffer 1 containing 10 nM capture probe; 100 nM detector probe; 50 nM target oligonucleotide); 2 hours at a flow rate of 10 μL/min;
e. 2000 μL Buffer 1 at a flow rate of 500 μL/min;
f. Blocking Reagent; 6 min at a flow rate of 20 μL/min;
g. 1000 μL Buffer 1 at a flow rate of 500 μL/min;
h. Staining Reagent (streptavidin-conjugated horseradish peroxidase in a solution containing $NaH_2PO_4$, EDTA, NP40 and Tween-20)
i. 2000 μL Buffer 1 at a flow rate of 500 μL/min. Substrate (Luminol).

All steps were performed at ambient temperature with the exception of the 2 hour hybridization incubation that was conducted at 37° C. Images of the arrays were captured on an MGX® 1200CL Detection Station using a CCD camera.

TABLE 10

Combinations of Targets and Detector Probes Tested

| Chip | Figure Showing Results | Target Oligonucleotides | Capture Probes | Detector Probes |
|---|---|---|---|---|
| A | FIG. 7A | SEQ ID NOs: 54, 60 and 66 | SEQ ID NOs: 55, 61 and 67 | SEQ ID NOs: 56, 62 and 68 |
| B | FIG. 7B | None | SEQ ID NOs: 55, 61 and 67 | SEQ ID NOs: 56, 62 and 68 |
| C | FIG. 7C | SEQ ID NO: 54 | SEQ ID NOs: 55, 61 and 67 | SEQ ID NOs: 56, 62 and 68 |
| D | FIG. 7D | SEQ ID NO: 60 | SEQ ID NOs: 55, 61 and 67 | SEQ ID NOs: 56, 62 and 68 |
| E | FIG. 7E | SEQ ID NO: 66 | SEQ ID NOs: 55, 61 and 67 | SEQ ID NOs: 56, 62 and 68 |

Results are depicted in FIGS. 7A-E. On Chip A (FIG. 7A), *E. coli*-, *S. aureus*- and *S. epidermidis*-based DNA oligonucleotides were detected simultaneously. Chip B (FIG. 7A) comprised a negative control without target oligonucleotides and yielded only low background signals. Chips C, D and E (FIGS. 7C-E, respectively) demonstrated specific detection of each of the three pathogenic organisms independently. There was no cross-reaction between capture and detection systems for any of the three organisms, thereby demonstrating the ability to discriminate these species using the probes and methods of the invention.

Example 5

A Prophetic Example of Specific Detection of *E. Coli*, *S. Aureus*, and *S. epidermidis* from Whole Blood Using ssrA or Rnase P RNAs as Targets Sample processing: A 10-ml volume of anticoagulated whole human blood is seeded with 10,000 organisms each of *S. aureus, S. epidermidis* and *E. coli* and is treated with 1% (v/v) Triton X-100 for 10 minutes at ambient temperature. A density matrix is formed by diluting iodixanol (1.32 g/ml) to a density of 1.090 g/ml with Dulbecco's phosphate-buffered saline. The entire volume of lysed blood containing the aforementioned organisms is overlayered onto 15 ml of the density matrix. The organisms are separated from blood debris by centrifugation at 5440×g for 40 minutes at ambient temperature. At the end of the centrifugation step, the density matrix is decanted, and the resulting organism pellet is re-suspended in 100 µL of RNase-free water prior to the isolation of total RNA. The recovery of three organisms at this stage may be verified by growth on differential media, followed by biochemical identification.

Target Preparation: Total RNA from 100 µL of the bacterial suspension is prepared using a QIAGEN® RNeasy® kit (QIAGEN, GmbH). Total bacterial RNA is recovered and re-suspended in a final volume of 60 µL of RNase-free water. Optionally, the RNA is fragmented in a fragmentation buffer (40 mM Tris, 100 mM potassium acetate, 30 mM magnesium acetate, pH 8.0) at 95° C. for 30 minutes to reduce secondary structure of the RNA.

Analysis On MetriGenix® Chips: Custom DNA chips comprising specific DNA capture probes for ssrA or RNaseP RNAs from each of the target organisms, as well as other species of potential interest, are manufactured by MetriGenix (MGX®, MetriGenix, Inc., Maryland, USA). The hybridization and detection process may take place on an MGX® 2000 hybridization station. Each capture probe comprises a target-specific region (capture sequence) of about 20 bases in length, which is immobilized on the surface of the chip via a 5' 9-base linker that has the sequence TTT TAA AAT (SEQ ID NO:87). Capture probes for each target organism are focused in discrete areas of the chip ("spots") permitting specific detection and identification of each species present within a sample. Negative controls for non-specific hybridization are included in which only a phosphate-buffered saline solution is spotted on the chip. Biotin-labeled DNA oligonucleotides are also spotted directly on the surface to act as positive staining controls for the chemiluminescent detection reaction. As depicted in FIG. 5, biotin-labeled detection probes are about 50 nucleotides in length and are positioned downstream, i.e., 3' of the capture probes. Detection probes are mixed with varying amounts of the fragmented total RNA at a final concentration of 140 nM in hybridization buffer (4×SSPE, 2.5× Denhardt's solution, with or without 30% formamide, pH 7.7). The probe-target RNA mixture is incubated at 95° C. for five minutes and then placed in a 45° C. water-bath for 10 minutes before applying a total volume of 66 µL to the chip surface, which is pre-blocked with goat serum to reduce non-specific binding. The hybridization process occurs at 4° C., or room temperature, for 10 hours at a flow rate of 10 µL/minute. Streptavidin-horseradish peroxidase solution (1.25 pg/µL) is then used to flood the chip. The streptavidin molecules bind to the biotin labels on the detection probes that are, in turn, bound to the captured RNA target sequences. Unbound materials are removed by washing with 4×SSPE, pH 7.7.

Detection: Specific capture of the target RNA is visualized by chemiluminescence using an MGX® 1200CL Detection Station. In the presence of hydrogen peroxide, horseradish peroxidase catalyzes the oxidation of the substrate Luminol, resulting in the emission of light that is captured by a CCD camera. The signal is collected and analyzed by MetriSoft™ software that corrects the signal intensity against the local background.

Predicted Results: No signals are detected in spots corresponding to negative controls, while staining controls yield strong positive signals. Positive signals are also detected at positions corresponding to the specific organism(s) present in the original sample. There is no signal above background from spots corresponding to organisms not seeded into the original blood sample, i.e., spots corresponding to organisms other than *S. aureus, S. epidermidis* or *E. coli*.

Example 6

Specific Detection of Bacterial RNA Using Probes for 16S rRNA, tmRNA (ssrA Transcripts), and RNase-P Transcripts The following example demonstrates the specific detection of *E. coli* and *S. aureus* RNA using the MetriGenix MGX™ 4D™ DNA chip (MetriGenix, Inc., Maryland, USA).

Preparation Of Chips: MetriGenix® chips were spotted with capture probes of 27-33 nucleotides in length that were directed towards (1) transcript sequences of the *E. coli, S. aureus*, or *S. epidermidis* ssrA gene (which encodes transfer-messenger RNA ("tmRNA")); (2) transcript sequences of the *E. coli, S. aureus*, or *S. epidermidis* Ribonuclease P ("RNase P" or "rnp") gene; (3) *E. coli* 16S rRNA, (4) *Trichomonas vaginalis* 18S rRNA, or (5) *Candida albicans* 18S rRNA. In addition to an organism-specific capture sequence, each capture probe comprised a 9-mer immobilization sequence of 5'-TTT TAA AAT (SEQ ID NO:87), through which the capture probe was attached to the chip surface. The sequences of the capture probes, including the 5' immobilization sequences, are set forth in Table 11. The capture sequences of the capture probes are set forth in Table 12.

The locations of the capture probes immobilized on the chips are shown in FIG. 8A. As can be seen in FIG. 8A, in certain locations (labeled "buffer"), only buffer was spotted on the chip. These locations served as negative controls for non-specific hybridization. In other locations, (labeled "staining"), biotin-labeled DNA oligonucleotides were also spotted directly on the surface to act as positive staining controls for the chemiluminescent detection reaction. The sequence of the staining control oligonucleotide (SEQ ID NO:83) was as follows: 5'-CCC AGG GAG ACC AAA AGC-Biotin. Each of the chips used in this example (Chip Nos. 1-4) bore the indicated capture probes in the arrangement indicated in FIG. 8A.

TABLE 11

Sequences of Capture Probes Used in Example 6

| Probe Name | Target Organism | Target Gene | 5'-3' Probe Sequence | SEQ ID NO: |
|---|---|---|---|---|
| CP1 | E. coli | ssrA | TTT TAA AAT TCC TCG GTA CTA CAT GCT TAG | 72 |
| CP2 | S. aureus | ssrA | TTT TAA AAT TTG ATT AAG TTT CTT CTA AAC AGA | 73 |
| CP3 | S. epidermidis | ssrA | TTT TAA AAT CAT CAT GCT AAG CAA TAA ACA A | 74 |
| CP4 | E. coli | rnp | TTT TAA AAT GCA CTG GTC GTG GGT TTC | 75 |
| CP5 | S. aureus | rnp | TTT TAA AAT TTA CTC TAT CCA TAT CGA AAG ACT | 76 |
| CP6 | S. epidermidis | rnp | TTT TAA AAT CTA TTC TAA CCA TAT CCA ATG ACT | 77 |
| CP7 | E. coli | 16S rRNA | TTT TAA AAT AGT GTG GCT GGT CAT CCT | 78 |
| CP8 | Trichomonas vaginalis | 18S rRNA | TTT TAA AAT ATC CTG AAA GAC CCG AAG CCT GTC | 79 |
| CP9 | Candida albicans | 18S rRNA | TTT TAA AAT TTG TTC CTC GTT AAG GTA TTT ACA TTG TAC TC | 80 |

TABLE 12

Capture Sequences of Capture Probes Used in Example 6

| Part of Probe | Target Organism | Target Gene | 5'-3' Probe Sequence | SEQ ID NO: |
|---|---|---|---|---|
| CP1 | E. coli | ssrA | TCC TCG GTA CTA CAT GCT TAG | 6 |
| CP2 | S. aureus | ssrA | TTG ATT AAG TTT CTT CTA AAC AGA | 1 |
| CP3 | S. epidermidis | ssrA | CAT CAT GCT AAG CAA TAA ACA A | 8 |
| CP4 | E. coli | rnp | GCA CTG GTC GTG GGT TTC | 46 |
| CP5 | S. aureus | rnp | TTA CTC TAT CCA TAT CGA AAG ACT | 47 |
| CP6 | S. epidermidis | rnp | CTA TTC TAA CCA TAT CCA ATG ACT | 48 |
| CP7 | E. coli | 16S rRNA | AGT GTG GCT GGT CAT CCT | 52 |
| CP8 | Trichomonas vaginalis | 18S rRNA | ATC CTG AAA GAC CCG AAG CCT GTC | 81 |
| CP9 | Candida albicans | 18S rRNA | TTG TTC CTC GTT AAG GTA TTT ACA TTG TAC TC | 82 |

Application Of Target RNA: Total RNA was isolated from E. coli, S. aureus, and S. epidermidis using a QIAGEN®-based extraction protocol. RNA (1.5 µg) from each organism was added either alone or in combination to buffer containing 1×SSPE, 0.15M NaCl, 0.01M NaH$_2$PO$_4$, 0.001M EDTA), 2.5% Triton X-100 and used to flood replicate MetriGenix® chips essentially as described in Example 4. Hybridization took place over 10 hours at room temperature at a flow rate of 10 µL/min. The combinations in which the RNA was used are set forth below and in Table 13. Chips were washed twice with MES buffer containing 0.88M NaCl, 0.02M EDTA, 0.5% sarcosine, 33% formamide prior to staining.

Detection Of Captured RNA: Organism-specific 50-mer detector probes that were labeled at the 3' end with BioTEG (Biotin with a 15 atom tetra-ethyleneglycol spacer). The detector probes were washed over the chips in combinations set forth below and in Table 13. The sequences of the detector probes are set forth in Table 14. The 3' BioTEG labels attached to the detector probes are also shown in Table 14. Streptavidin-horseradish peroxidase solution (1.25 pg/µL) was then used to flood the chip. The streptavidin molecules bound to the biotin labels on the detection probes that were, in turn, bound to the captured RNA target sequences. Unbound materials were removed by washing with 1×MES. Bound detector probes were visualized by chemiluminescence. Specifically, a chemiluminescent substrate (Luminol) was used to flood the chips. In the presence of hydrogen peroxide, horseradish peroxidase catalyzed the oxidation of the substrate Luminol, resulting in the emission of light that was captured by a CCD camera. The assays were performed on an MGX® 2000 hybridization station (MetriGenix, Inc., Maryland, USA). Images of the array were captured over a 10 second period using an MGX® 1200CL Detection Station (MetriGenix, Inc., Maryland, USA) equipped with a CCD camera. Results are depicted in FIGS. 8B-E.

and 16S rRNA transcript sequences (Eco_ssrA_DP50 (SEQ ID NO:43), Eco_Rnp_DP50 (SEQ ID NO:49), and Eco_16_DP50 (SEQ ID NO:53)). As can be seen in FIG. 8B, only the spots on the chip corresponding to the *E. coli*-specific target sequences and the positive staining controls yielded signals above background.

FIG. 8C is a CCD image depicting Chip No. 2 after performance of the assay described in this example. Chip No. 2 was flooded with total RNA from *S. aureus* and *S. epidermidis*. After washing to remove unbound RNA, the RNA immobilized on the chip was contacted with detector probes specific for *E. coli* ssrA, rnp and 16S rRNA transcript sequences (Eco_ssrA_DP50 (SEQ ID NO:43), Eco_Rnp_DP50 (SEQ ID NO:49), and Eco_16_DP50 (SEQ ID NO:53)). As can be

TABLE 13

Combinations of Targets and Detector Probes Tested in Example 6

Figure 8D:
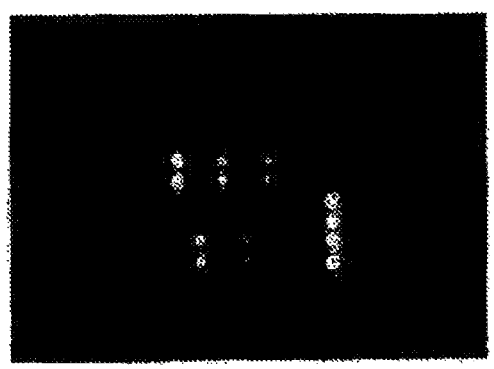
Figure 8E:
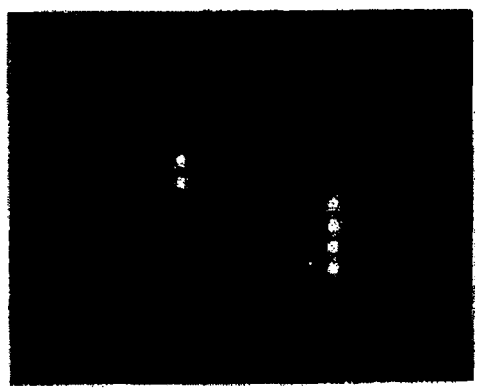

| Chip No. | Figure Showing Results | Target Organisms | Detector Probes Contacted with RNA from Target Organism Immobilized on Chip |
|---|---|---|---|
| 1 | FIG. 8B | *E. coli* | Eco_ssrA_DP50 (specific for *E. coli* ssrA) |
|   |         |           | Eco_rnp_DP50 (specific for *E. coli* rnp) |
|   |         |           | Eco_16_DP50 (specific for *E. coli* 16S rRNA) |
| 2 | FIG. 8C | *S. aureus* | Eco_ssrA_DP50 (specific for *E. coli* ssrA) |
|   |         | *S. epidermidis* | Eco_rnp_DP50 (specific for *E. coli* rnp) |
|   |         |           | Eco_16_DP50 (specific for *E. coli* 16S rRNA) |
| 3 | FIG. 8D | *S. aureus* | Sau_ssrA_DP50 (specific for *S. aureus* ssrA) |
|   |         |           | Sau_rnp_DP50 (specific for *S. aureus* rnp) |
| 4 | FIG. 8E | *E. coli* | Sau_ssrA_DP50 (specific for *S. aureus* ssrA) |
|   |         | *S. epidermidis* | Sau_rnp_DP50 (specific for *S. aureus* rnp) |

TABLE 14

Sequences of Detector Probes Used in Example 6

| Probe Name | Target Organism | Target Gene | 5'-3' Probe Sequence | SEQ ID NO: labeled with BioTEG[†] |
|---|---|---|---|---|
| Eco_ssrA_DP50 | *E. coli* | ssrA | TCA GTC TTT ACA TTC GCT TGC CAG CTG CGG ACG GAC ACG CCA CTA ACA AA-BioTEG | 43 |
| Sau_ssrA_DP50 | *S. aureus* | ssrA | CTT CAA ACG GCA GTG TTT AGC ATA TCC TAT TAA GGT TGA ATC GCG TTA AC-BioTEG | 44 |
| Eco_rnp_DP50 | *E. coli* | rnp | CCC CCC AGG CGT TAC CTG GCA CCC TGC CCT ATG GAG CCC GGA CTT TCC TC-BioTEG | 49 |
| Sau_rnp_DP50 | *S. aureus* | rnp | TAG GAT ATT TCA TTG CCG TCA AAT TAA TGC CTT GAT TTA TTG TTT CAT CA-BioTEG | 50 |
| Eco_16_DP50 | *E. coli* | 16S rRNA | CTC AGA CCA GCT AGG GAT CGT CGC CTT GGT GAG CCG TTA CCC CAC CAA CA-BioTEG | 53 |

[†]BioTEG = 3' Biotin with a 15 atom tetra-ethyleneglycol spacer

FIG. 8B is a CCD image depicting Chip No. 1 after performance of the assay described in this example. Chip No. 1 was flooded with total RNA from *E. coli*. After washing to remove unbound RNA, the immobilized RNA on the chip was contacted with detector probes specific for *E. coli* ssrA, rnp seen in FIG. 8C, only the spots on the chip corresponding to the positive staining controls yielded signals above background.

FIG. 8D is a CCD image depicting Chip No. 3 after performance of the assay described in this example. Chip No. 3 was flooded with total RNA from *S. aureus*. After washing to remove unbound RNA, the immobilized RNA on the chip was contacted with detector probes specific for *S. aureus* ssrA and rnp transcript sequences (Sau_ssrA_DP50 (SEQ ID NO:44) and Sau_Rnp_DP50 (SEQ ID NO:50)). As can be seen in FIG. 8D, only the spots on the chip corresponding to the *S. aureus*-specific target sequences and the positive staining controls yielded signals above background.

FIG. 8E is a CCD image depicting Chip No. 4 after performance of the assay described in this example. Chip No. 4 was flooded with total RNA from *E. coli* and *S. epidermidis*. After washing to remove unbound RNA, the immobilized RNA on the chip was contacted with detector probes specific for *S. aureus* ssrA and rnp transcript sequences (Sau_ssrA_DP50 (SEQ ID NO:44) and Sau_Rnp_DP50 (SEQ ID NO:50)). As can be seen in FIG. 8E, only the spots on the chip corresponding to the positive staining controls yielded signals above background.

For all combinations studied, no signals were detected in spots corresponding to negative controls, while staining controls yielded strong positive signals. Strong positive signals were also detected at spots bearing immobilized RNA derived from a given specific organism when detector probes specific for that organism were contacted to the immobilized RNA on the chip. No signals were detected at spots bearing RNA derived from a given specific organism when no detector probes specific for that organism were contacted to the immobilized RNA on the chip. Contacting RNA derived from a given specific organism with detector probe(s) specific for different organism(s) produced no signals. These data demonstrate that both the capture probes and the detector probes used were able to selectively bind to specific target RNA. There was no cross-reaction between capture and detection systems for any of the three organisms, thereby demonstrating the ability to discriminate these species using the probes and methods of the invention.

There is no signal above background from spots corresponding to organisms not seeded into the original sample, i.e., spots corresponding to organisms other than *S. aureus, S. epidermidis* or *E. coli*.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents.

What is claimed is:

1. A method for detecting the presence of *Staphylococcus aureus* in a sample, the method comprising:
   (a) releasing RNA or DNA from at least one microorganism in the sample;
   (b) contacting the RNA or DNA with at least one capture probe capable of hybridizing to a first target sequence of the RNA or DNA, wherein the contacting is performed under conditions that permit hybridization between the first target sequence and the at least one capture probe to form a RNA- or DNA-capture probe hybrid complex, and wherein the at least one capture probe comprises at least one sequence selected from the group consisting of SEQ ID NOs: 73 and 76; and
   (c) detecting the presence of the RNA- or DNA-capture probe hybrid complex by
   (i) contacting the RNA or DNA with at least one detector probe capable of hybridizing to a second target sequence of the RNA or DNA, wherein the detector probe comprises at least one reporter group and wherein the contacting is performed under conditions that permit hybridization between the second target sequence and the at least one detector probe to form a RNA- or DNA-capture probe-detector probe hybrid complex, and wherein the at least one detector probe comprises at least one sequence selected from the group consisting of SEQ ID NOs: 1, 2, 44, 47, 50, 61, 62, 73, and 76; and
   (ii) detecting the RNA- or DNA-capture probe-detector probe hybrid complex by detecting the at least one reporter group wherein the presence of the RNA- or DNA-capture probe-detector probe hybrid complex indicates the presence of *Staphylococcus aureus*.

2. The method of claim 1, wherein the first target sequence and the second target sequence comprise the same sequence.

3. The method of claim 1, wherein the capture probe is immobilized on a solid support before hybridizing to the first target sequence.

4. The method of claim 1, wherein the RNA- or DNA-capture probe hybrid complex is immobilized on a solid support.

5. The method of claim 1, wherein the RNA- or DNA-capture probe-detector probe hybrid complex is immobilized on a solid support.

6. The method of any one of claims 3, 4, and 5, wherein the solid support is selected from the group consisting of latex beads, agarose beads, paramagnetic beads, ferric oxide, microarray chips, filter paper, nitrocellulose filters, nylon membranes, glass slides and cellular membranes.

7. The method of claim 6, wherein the solid support is a microarray chip.

8. The method of claim 3, wherein two or more capture probes are immobilized on a single spot of the solid support.

9. The method of claim 3, further comprising an immobilization probe that is capable of hybridizing to the capture probe to be immobilized onto the solid support.

10. The method of claim 1, wherein the reporter group is selected from the group consisting of a radioactive isotope, an enzyme, a fluorescent molecule and an amplification sequence.

11. The method of claim 10, wherein the amplification sequence initiates an amplification reaction selected from the group consisting of strand displacement amplification (SDA), polymerase chain reaction (PCR), reverse transcriptase-strand displacement amplification (RT-SDA), reverse transcriptasepolymerase chain reaction (RT-PCR), nucleic acid sequence based amplification (NASBA), transcription-mediated amplification (TMA), rolling circle amplification and Qβ replicase amplification.

12. The method of claim 1, wherein detection of the RNA- or DNA capture probe-detector probe hybrid complex is accomplished via non-specifically labeling the hybrid complex.

13. The method of claim 1, wherein the at least one detector probe is selected from the group consisting of SEQ ID NOs: 44 and 50.

14. A method for detecting the presence of *Staphylococcus aureus* in a sample, the method comprising:
   (a) releasing RNA or DNA from at least one microorganism in the sample;
   (b) contacting the RNA or DNA with at least one capture probe capable of hybridizing to a first target sequence of the RNA or DNA, wherein the contacting is performed under conditions that permit hybridization between the first target sequence and the at least one capture probe to form a RNA- or DNA-capture probe hybrid complex, and wherein the at least one capture probe comprises at least one sequence selected from the group consisting of SEQ ID NOs: 1, 2, 44, 47, 50, 61, 62, 73, and 76; and
   (c) detecting the presence of the RNA- or DNA-capture probe hybrid complex by
      (i) contacting the RNA or DNA with at least one detector probe capable of hybridizing to a second target sequence of the RNA or DNA, wherein the detector probe comprises at least one reporter group and wherein the contacting is performed under conditions that permit hybridization between the second target sequence and the at least one detector probe to form a RNA- or DNA-capture probe-detector probe hybrid complex, and wherein the at least one detector probe comprises at least one sequence selected from the group consisting of SEQ ID NOs: 73 and 76; and
      (ii) detecting the RNA- or DNA-capture probe-detector probe hybrid complex by detecting the at least one reporter group wherein the presence of the RNA- or DNA capture probe-detector probe hybrid complex indicates the presence of *Staphylococcus aureus*.

15. The method of claim 14, wherein the first target sequence and the second target sequence comprise the same sequence.

16. The method of claim 14, wherein the capture probe is immobilized on a solid support before hybridizing to the first target sequence.

17. The method of claim 14, wherein the RNA- or DNA-capture probe hybrid complex is immobilized on a solid support.

18. The method of claim 14, wherein the RNA- or DNA-capture probe-detector probe hybrid complex is immobilized on a solid support.

19. The method of any one of claims 16, 17, and 18, wherein the solid support is selected from the group consisting of latex beads, agarose beads, paramagnetic beads, ferric oxide, microarray chips, filter paper, nitrocellulose filters, nylon membranes, glass slides and cellular membranes.

20. The method of claim 19, wherein the solid support is a microarray chip.

21. The method of claim 16, wherein two or more capture probes are immobilized on a single spot of the solid support.

22. The method of claim 16, further comprising an immobilization probe that is capable of hybridizing to the capture probe to be immobilized onto the solid support.

23. The method of claim 14, wherein the reporter group is selected from the group consisting of a radioactive isotope, an enzyme, a fluorescent molecule and an amplification sequence.

24. The method of claim 23, wherein the amplification sequence initiates an amplification reaction selected from the group consisting of strand displacement amplification (SDA), polymerase chain reaction (PCR), reverse transcriptase-strand displacement amplification (RT-SDA), reverse transcriptasepolymerase chain reaction (RT-PCR), nucleic acid sequence based amplification (NASBA), transcription-mediated amplification (TMA), rolling circle amplification and Qβ replicase amplification.

25. The method of claim 14, wherein detection of the RNA- or DNA-capture probe-detector probe hybrid complex is accomplished via non-specifically labeling the hybrid complex.

26. The method of claim 14, wherein the at least one capture probe is selected from the group consisting of SEQ ID NOs: 44 and 50.

* * * * *